United States Patent [19]

Shewmaker et al.

[11] Patent Number: 5,177,011

[45] Date of Patent: Jan. 5, 1993

[54] PLANT ELONGATION FACTOR PROMOTERS, CODING SEQUENCES AND USES

[75] Inventors: Christine K. Shewmaker, Woodland; William R. Hiatt, Davis, both of Calif.; Ann R. Pokalsky, Brooklyn, N.Y.

[73] Assignee: Calgene, Inc., Davis, Calif.

[21] Appl. No.: 637,990

[22] Filed: Jan. 3, 1991

Related U.S. Application Data

[63] Continuation of Ser. No. 393,366, Aug. 18, 1989, abandoned, which is a continuation-in-part of Ser. No. 335,133, Apr. 7, 1989, abandoned, which is a continuation-in-part of Ser. No. 234,187, Aug. 18, 1988, abandoned.

[51] Int. Cl.$^5$ .................... C12N 15/67; C12N 15/82; C12N 15/29
[52] U.S. Cl. .................... 435/172.3; 435/172.1; 435/240.4; 435/317.1; 536/23.6; 536/24.1; 800/205; 935/35; 935/64
[58] Field of Search ........... 435/172.1, 172.3, 240.4, 435/317.1; 800/205; 536/27; 935/35, 64

[56] References Cited

U.S. PATENT DOCUMENTS 4,394,443  7/1983  Weissman et al. .................... 435/68
4,446,235  5/1984  Seeburg ............................ 435/91
4,656,131  4/0787  Kitano et al. .

OTHER PUBLICATIONS

Lauer et al., 1984. J. Biol. Chem 259(3):1644–1648.
Pokalsky et al., "Structure and expression of elongation factor 1α in tomato," Nucleic acids Research (1989) 17:4661–4673.
Uetsuki et al., "Isolation and Characterization of the Human Chromosomal Gene for Polypeptide Chain Elongation Factor-1α," Journal of Biological Chemistry (1989) 10:5791–5798.
Linz et al., "Expression of Three Genes for Elongation Factor 1α During Morphogenesis of Mucor racemosus," Molecular and Cellular Biology (1987) 7:1926–1932.
Opdenakker et al., "Human elongation factor 1α: a polymorphic and conserved multigene family with multiple chromosomal localizations," Human Genetics (1987) 75:339–344.
Kohl et al., "Hsp90, hsc73 and EF-1α gene expression in non-heatshocked and heatshocked LMTK⁻ cells," Nucleic Acids Research (1987) vol. 15, No. 16, p. 6756.
Linz et al., "Three Genes for the elongation Factor EF-1α in Mucor racemosus," Molecular and Cellular Biology (1986a) 6:593–600.
Lenstra et al., "Genes coding for the elongation factor EF-1α in Artemia," European Journal of Biochemistry (1986) 155:475–483.
Brands et al., "The primary structure of the α subunit of human elongation factor 1: Structural aspects of guanine-nucleotide-binding sites," European Journal of Biochemistry (1986) 155:167–171.
Nagashima et al., "Structure of the two genes coding for polypeptide chain elongation factor 1α (EF-1α) from Saccharomyces cerevisiae," Gene (1986) 45:265–273.
Ejiri, "Purification and Characterization of Polypeptide Chain Elongation Factor 1 from Plants," Methods in Enzymology (1986) 118:140–153.
Linz et al., "The Primary Structure and the Functional Domains of an Elongation Factor-1α from Mucor racemosus," Journal of Bio. Chem. (1986b) 261:15022–15029.

(List continued on next page.)

Primary Examiner—Elizabeth C. Weimar
Assistant Examiner—P. R. Rhodes

[57] ABSTRACT

Expression constructs are provided employing a plant EF-1α promote which allows for elevated expression in rapidly dividing cells. Sequences from the gene and untranslated regions associated with the gene may be employed in an antisense construct to reduce growth rate. The promoter finds particular use in protecting rapidly dividing tissue and tender shoots from a wide variety of environmentally induced stress conditions.

2 Claims, 31 Drawing Sheets

OTHER PUBLICATIONS

Daum et al., "The Expression of a Gene for Eukaryotic Elongation Factor Tu in Artemia During Development: Translation of Poly (A)⁻ RNA and the Use of Synthetic Oligonucleotide to Detect the Presence of Eukaryotic Elongation Factor Tu-Specific mRNA," *Journal of Bio. Chem.* (1985) 260:16347-16353.

Fonzi et al., "Regulation of Protein Synthesis Factor EF-1α in *Mucor racemosus*," *Molecular and Cellular Biology* (1985) 5:1100-1103.

Thiele et al., "Elongation Factor 1α from *Saccharomyces cerevisiae*: Rapid large-scale purification and molecular characterization," *Journal of Bio. Chem.* (1985) 260:3084-3089.

Tuhackova et al., "Regulation of the activity of eukaryotic peptide elongation factor 1 by autocatalytic phosphorylation," *Eur. J. Biochem.* (1985) 146:161-166.

Nagata et al., "Polypeptide chain elongation factor 1α (EF-1α) from yeast: nucleotide sequence of one of the two genes for EF-1α from *Saccharomyces cerevisiae*," *EMBO Journal* (1984) 3:1825-1830.

van Hemert et al., "Polypeptide chain elongation factor EF-1α from the brine shrimp Artemia," *EMBO Journal* (1984) 3:1109-1113.

Webster and Webster, "Specific Disappearance of Translatable Messenger RNA for Elongation Factor One in Aging *Drosophila melanogaster*," *Mechanisms of Ageing and Development* (1984) 24:335-342.

van Hemert et al., "Genes for elongation factor EF-1α in the brine shrimp Artemia," *FEBS* (1983) 157:295-299.

Hiatt et al., "Methylation of elongation factor 1α from the fungus Mucor," *PNAS* (1982) 79:3433-3437.

Slobin et al., "Functional and Structural Studies on a Tryptic Fragment of Eucaryotic Elongation Factor Tu from Rabbit Reticulocytes," *Biochemistry* (1982) 20:5761-5767.

Slobin, "The Role of Eucaryotic Elongation Factor Tu in Protein Synthesis: The Measurement of the Elongation Factor Tu Content of Rabbit Reticulocytes and Other Mammalian Cells by a Sensitive Radioimmunoassay," *Eur. J. Biochem* (1980) 110:555-563.

Riis et al., "Eukaryotic Protein Elongation Factors," *Trends in Biochemical Sciences* (1990) 15:420-424.

Shepherd et al., "Fruit Flies with Additional Expression of the Elongation Factor EF-1α Live Longer," *Proc. Natl. Acad. Sci.* (1989) 86:7520-7521.

Cottrell et al., "Either One of the Two Yeast EF-1α Genes is Required For Cell Viability," *Current Genetics* (1985) 9:693-697.

Rothstein et al., "Promoter cassettes, antibiotic-resistance genes, and vectors for plant transformation," *Gene* (1987) 53:153-161.

Lenstra et al., "Genes coding for the elongation of EF-1α in Artemia," *Eur. J. Biochem.* (1986) 155:475-483.

Rodermel et al., "Nuclear-Organelle Interactions: Nuclear Antisense Gene Inhibits Ribulose Bisphosphate Carboxylase Enzyme Levels in Transformed Tobacco Plants," *Cell* (1988) 55:673-681.

Ting, "Growth, Growth Kinetics, and Growth Movements," *Plant Physiology* (1982) Chapter 17, pp. 459-462.

Okamuro and Goldberg, "Regulation of Plant Gene Expression: General Principles," *The Biochem. of Plants, A comprehensive Treatise* (1989) pp. 1-3.

Axelos et al., "The gene family encoding the *Arabidopsis thaliana* translation elongation factor EF-1α: Molecular cloning, characterization and expression," *Mol. Gen. Genet.* (1989) 219:106-112.

Hovemann et al., "Two genes encode related cytoplasmic elongation factors 1α (EF-1α) in *Drosophila melanogaster* with continuous and stage specific expression," *Nucleic Acids Research* (1988) vol. 16, No. 8 pp. 3175-3194.

```
CTCCTCAGCTGTGCCGCATATCGCCTAATTTTCTTCTCTAAGTTTCTTAGTGTCTCAAG ATG GGT AAA GAG AAG ATT CAC   81
                                                          M   G   K   E   K   I   H     7

ATC AGC ATT GTG GTC ATT GGT CAT GTT GAC TCT GGA AAG TCG ACT ACC ACT GGT CAC TTG ATC TAC AAG  150
 I   S   I   V   V   I   G   H   V   D   S   G   K   S   T   T   T   G   H   L   I   Y   K   30

CTT GGT ATT GAC AAG CGT GTT ATT GAG AGG TTC GAG AAA GAA GCT GCT GAG ATG AAC AAG AGG TCA  219
 L   G   I   D   K   R   V   I   E   R   F   E   K   E   A   A   E   M   N   K   R   S    53

TTC AAG TAT GCC TGG GTG CTT GAC AAA CTT AAG TAC TGC TAC ACT GTT ATT GAT GCC ATT GAT ATT GCT  288
 F   K   Y   A   W   V   L   D   K   L   K   Y   C   Y   T   V   I   D   A   I   D   I   A   76

TTG TGG AAG TTT GAG ACC ACT GGT ACC TCT CAG GCT GAC TGT GCT GTT CTC ATT ATT GAC TCC ACT GGT GGT  357
 L   W   K   F   E   T   T   G   T   S   Q   A   D   C   A   V   L   I   I   D   S   T   G   99

AAG AAC ATG ATC ACT GGT ATC TCC AAA GAT GGT CAG ACC CGT GAA CAT GCA TTG CTT GCT TTC ACC CTT GGT GTC  426
 K   N   M   I   T   G   I   S   K   D   G   Q   T   R   E   H   A   L   L   A   F   T   L   G   V  122

TTT GAA GCT GGT ATC TCC AAA GAT GGT CAG ACC CGT GAA CAT GCA TTG CTT GCT TTC ACC CTT GGT GTC  495
 F   E   A   G   I   S   K   D   G   Q   T   R   E   H   A   L   L   A   F   T   L   G   V  145

AAG CAA ATG ATC TGC TGT AAC AAG ATG GAT GCT ACC ACC CCC AAG TAC TCC AAG GCT AGG TAT GAT  564
 K   Q   M   I   C   C   N   K   M   D   A   T   T   P   K   Y   S   K   A   R   Y   D   168
```

FIGURE 1A

```
GAA ATC GTG AAG GAA GTT TCT TCC TAC CTC AAG AAG GTT GGT TAC AAC CCT GAC AAA ATC CCC TTT GTT    633
 E   I   V   K   E   V   S   S   Y   L   K   K   V   G   Y   N   P   D   K   I   P   F   V     191

CCA ATC TCT GGT TTT GAA GGA GAC AAC ATG ATT GAG AGG TCT ACC AAC CTC GAC TGG TAC AAG GGA CCA    702
 P   I   S   G   F   E   G   D   N   M   I   E   R   S   T   N   L   D   W   Y   K   G   P     214

ACC CTC CTT GAG GCT CTT GAC CAG ATT AAC GAG CCC AAG AGG CCA TCA GAC AAA CCC CTC CGT CTT CCA    771
 T   L   L   E   A   L   D   Q   I   N   E   P   K   R   P   S   D   K   P   L   R   L   P     237

CTT CAG GAT GTT TAC AAG ATT GGT GTG ACT GTC CCT GTT GGT CGC GTT GAG ACT GGT GTG ATC            840
 L   Q   D   V   Y   K   I   G   V   T   V   P   V   G   R   V   E   T   G   V   I             260

AAG CCT GGT ATG GTT GTG ACC TTT GGC ATT GGA CCT TTG ACA ACT GAA GTC AAG TCT GTT GAG ATG CAC    909
 K   P   G   M   V   V   T   F   G   I   G   P   L   T   T   E   V   K   S   V   E   M   H     283

CAC GAA GCT CTC CAG GAG GCA CTC CCT GGT GAC AAT GTT GGG TTC AAT GTT AAT GTT GCT GTT AAG        978
 H   E   A   L   Q   E   A   L   P   G   D   N   V   G   F   N   V   K   N   V   A   V   K     306

GAT CTT AAG CGT GGT TAT GTT GCC TCA AAC TCC AAG GAT GAC CCA GCC AAG GGG GCA GCC AGC TTC ACT    1047
 D   L   K   R   G   Y   V   A   S   N   S   K   D   D   P   A   K   G   A   A   S   F   T     329

GCC CAG GTC ATC ATC ATG AAC CAT CCT GGC CAG ATT GGA AAT GGA TAT GCT CCA GTG CTT GAT TGT CAC    1116
 A   Q   V   I   I   M   N   H   P   G   Q   I   G   N   G   Y   A   P   V   L   D   C   H     352
```

FIGURE 1B

```
ACT TCC CAC ATT GCT GTC AAG TTT GCT GAG ATC TTG ACC AAG ATT GAC AGG CGT TCA GGT AAG GAA CTT  1185
 T   S   H   I   A   V   K   F   A   E   I   L   T   K   I   D   R   R   S   G   K   E   L    375

GAG AAG GAG CCT AAG TTC TTG AAG AAC GGT GAT GCT GGT ATG GTT AAG ATT CCC ACC AAG CCC ATG  1254
 E   K   E   P   K   F   L   K   N   G   D   A   G   M   V   K   I   P   T   K   P   M    398

GTT GAG ACC TTT GCT GAA TAC CCT CCA TTG GGT CGT TTT GCT GTG AGG GAC ATG AGG CAG ACT GTT  1323
 V   E   T   F   A   E   Y   P   P   L   G   R   F   A   V   R   D   M   R   Q   T   V    421

GCT GTT GGT GTT GTC AAG AAT GTT GAC AAG AAG GAC CCA ACT GGT GCC AAG GTG ACC AAG GCT GCC CAG  1392
 A   V   G   V   V   K   N   V   D   K   K   D   P   T   G   A   K   V   T   K   A   A   Q    444

AAG AAG GGG AAG TGA ACTGTGCAGTGTGATGCTGGTGTTTCGAATGCTATTATTACATCGAGTGTGCTATCTAGACTCTGTTTT  1478
 K   K   G   K   *                                                                            448

ATTTAATTCGCTTAGTTTGGTCTTTGAGTTGTGGTTCTCTGACTTGTCTGTCAAGTATCCATTCTCAGAACTGGGTA  1569

CTTGATAGGCGGTGGCGAGCATGATTTGAGTCTGTTATCATTTGCTTTGTTGAGTGCCTTGTTTGTTTCCATGGTGCTCGGGATT  1660

TTTGTTGCTTTAATTTGAGATTAAGTTTTCT-(POLY-A TAIL)
    1692
```

FIGURE 1C

```
  1  MGKEKIHISIVVIGHVDSGKSTTTGHLIYKLGGIDKRVIEFEKEAALNMSFKYAWVLDKLKAERERGIT     1
  1  MGKEKIHINIVVIGHVDSGKSTTTGHLIYKCGIDKRTIEKFEKEAQEMGKSFKYAWVLDKLKAERERGIT    2
  1  MGKEKTHINIVVIGHVDSGKSTTTGHLIYKQGIDKRTIEKFEKEAEMGKSFKYAWVLDKLKAERERGIT     3
  1  MGKEKTHVNVVVIGHVDSGKSTTTGHLIYKCGIDKRTIEPFEKEAAELGKGSFKYAWLDKLKAERERGIT    4
  1  MGKEKSHINVVVIGHVDSGKSTTTGHLIYKQGGIDKRTIEKFEKEAAELGKSFKYAWVLDKLKAERERGIT   5

73  IDIALWKFETIKYYQTVIDAPGHRDFIKNMITGTSQADCAVLIIDSTLGFEAGISKDGQTREHALLAFTLG   1
 73  IDIALWKFETAKYYVTLIDAPGHRDFIKNMITGTSQADCAVLIVAAGVGEFEAGISKNGQTREHALLAFTLG 2
 73  IDISLWKFETIKYYVHILDAPGHRDFIKNMITGTSQADCAVLIVAAGVGEFEAGISKNGQTREHALLAFTLG 3
 73  IDIALWKFETPKYNVTVIDAPGHRDFIKNMITGTSQADCALLIIAGGTGEFEAGISKDGQTREHALLAFTLG 4
 73  IDIALWKFEJFKYQVIVIDAPGHRDFIKNMITGTSQADCAILIIAGGVGEFEAGISKDGQTREHALLAFTLG 5

145  VKQMICCCONKMDATTPKYSKARYDEIVKEVSSYLKKVGYNPDKIPFVPISQFEGDNMIEHSTNILWYKG   1
145  VKQLIVGVNKMDSTEPPYSEQRFEEIKKEVSAYIKKIDYNFAAVAFVPISGWEGDNMLEASDRLPWYKGWNI 2
145  VKQLIVGVNKMDSTEDKYSQKRYEEIVKEVSMYIKKIGYNPTVAFVPISGWNGDNMLEPSANMFWKGWKV   3
145  FRQLIVAINKMDTIKWSDRYNEIVKEVSGFIKKLGNEKSVPFVPISGWEGDNMLDESTNMEWYKGWNK    4
145  VRQLIVAVNKMDSVKWDESEFQEIVKETTNFIKKVGYNEKTVPFVPISGWNGDNMIEATINAFWYKGWEK   5

214  PTILEADQINEKPSWPLRLPLQDVFNVAVKDLPFVPISQFEGDNMIEHSTNIL WYKG   1
217  ERKEGKADGKTLIDALDAILPETRPTDKPLRLPLQDVYKIGGIGTVPGRVETGVIKPGMVVTFAPANITTE 2
217  TRKDGNASGTTLLEALDCILPETRPTDKPLRLPLQDVYKIGGIGTVPGRVETGVIKPGMVTFAPANITTE  3
215  ETKAGSKTGKTLLEAIDAEPTVRPSDRLRLPLQDVYKIGGIGTVPGRVETGVIKPGMVTFAPAAVTTE    4
215  ETKAGVVKGKTLLEALDAUEGSRFTDKPLRLPLQDVYKIGGIGTVPGRVETGVIKPGMVTFAPAGVTTE   5

277  VKSVEMHHEALOEALPGDNVGFNVKNVAVKDLARGYVASNSKPDPAKGAASFTAQVINHPGQINGYAPV   1
289  VKSVEMHHESLEGAPGDNVGFNVKNVSVKLPRGYVAGDSKNPARCSDPFAAGFTAQVINHPGQISNGYPV  2
289  VKSVEMHHEHHEALSEALPGDNVGFNVKNVSVKURGNVAGDSKNDPEMEAAGFTAQVINHPGQISAGYAPV 3
287  VKSVEMHHETIEGLPGDNVGFNVKNVSVKDIRRGNVEBDSKNDPAKESASFTAQVIIGMVVNFAPAAVTTE 4
287  VKSVEMHHEQLEQGVPGDNVGFNVKNVSVKEIRRGNVCGDAKIDPFKGCASFNATIVILVFAPAGVTTE   5

349  LDCHTSHIAVKFAEILIKIDRRSGKFLEKEPKFANGDAGMVKNFKPMIVETFAEYPPLGRFAVRMRQT    1
361  LDCHTAHIACKFAEJEKODRRLIEKIDRRSGKLEDGPKFLKSDAAMITLVESKFLCVEAFSDFPPLGRFAVRDMRQT 2
361  LDCHTAHIACKFAELKEKIDRRSGKLEDGPKFLKSDEAIVKMVPCKPMOVESDAYPPLGRFAVRDMRQT  3
359  LDCHTAHIACKFSGLIEKIDRRSGKKMDDSPKFLKSDSAIVKMVKPSKPMVEAYTDMPPLGRFAVRDMRQT 4
359  LDCHTAHIACREMIEFELKSGDAAUVFFVPSKPMCVENFSEYPPLGRFAVRDMRQT               5

421  VAVGMVKNVDKKDPTGAKVTKAAQKGK       1
433  VAVGVIKSVMEKDPTAGKVTKAAADAGKK     2
433  VAVGVIKAVDKPAAGAGKVTKQAQKAK       3
431  VAVGVIKAMEKVDKACGKVTKAAADASKK     4
431  VAVGVIKSMDKTEKAAKVTKAAQKAKK       5
```

FIGURE 2

```
  1 TATTATTATAAAAAAAACTACCGACTAAGCTCATTCATCCCTCCTCTATATATACCAATAACC  69

70 TCTTGTAAACTTAAATAAAGTTCCTTCATTTTCAACTTAATATGTGCTGTGCCTTCTCTAGTTA 138

139 GATATATATATTGATATTCCATCACTCATTTTTGCTTATTTTATGTAAAATTCATGCAAATTGTTCC 207

208 ATGATCCATCAGTTTTAATAAAATTGATACTAGATAGTGTAATTGGTGATGCAAATTGGTGATGTTG 276

277 CTGAGTTTATATAATTAATAGGCTGTGTTGATCCGTTCATTTTATATATCTTTTCTTTTCGTCTG 345

346 TCTCAAAAAGATGTCACTTTATTATGAGAAATAATTACTAAAAACTTCATTTTTACACGTAATGAAT 414
                                                                    DraI
                                                                     |
415 TGATTTATTGCTACATAAATATTTAAGTATTGCTTTGAACTATAAATATCGTTCTTTTAAATATTATGT 483
                                                              473
```

FIGURE 3A

```
                                              ScaI
                                               |
484  CAAGTCAAAATTGTCACGTGAAATGAGACAGAGTGAGTACTGGTTTTATTGTTGCTTTCTGTTT  552
                                              524

553  CTATATATTTGATAGTAGCTTGGATTAATTAACTCAAGATTTGTGACTAAAGTTCATTAGTTTTGTTC  621

XbaI
                               |
622  ATCTTAAATGTCTCATAATTCCTGGAGAAGGATGCTTGCCTTCTAGATTGTTCAGTCTGTGTATTGTTT  690
                                       664

BclI
      |
691  GATCATTGTTGGATGATCTGTTCGTTGATTGGCTACCTAAACTCGATTTGATGTATTCGATTTTCA  759
     691

AccI
                                          |
760  GAATTTCTCTATGTTTTGTGTGAATATCAGATTGTTGTAGACATAGAACACAACTTTTAGATGTATTTG  828
                                         798
```

FIGURE 3B

```
                          HincII        BclI
                          ‾‾‾‾‾‾        ‾‾‾‾
829  ACATTTGTTTCTATTGTGACAAGACTTCTAGTTGATCAACAAGGTAAAGAGAAGGTTCACATCAACA  897
                                            863  METGlyLysGluLysValHisIleAsnI HincII
                       ‾‾‾‾‾‾
              BalI
              ‾‾‾‾
898  TTGTGGTTATTGGCCATGTGACTCTGGCAAATCGACTACCACCTGGTCACTTGATCTACAAGCTAGGTG  966
     leValValIleGlyHisValAspSerGlyLysSerThrThrThrGlyHisLeuIleTyrLysLeuGlyG
                                               911 915

ClaI
       ‾‾‾‾
967  GTATCGATAAACGTGTCATCGAGAGTTTGAGAAAGAAGCTGCTGAGATGAACAAGAGGTCATTCAAGT  1035
     lyIleAspLysArgValIleGluArgPheGluLysGluLeuLeuArgMETAsnLysArgSerPheLysT
     971

1036 ATGCCTGGGTTCTTGACAAGCTCAAGGCTGAACGTGAACGGGTATCACTATTGATATTGCCTTGTGGA  1104
     yrAlaTrpValLeuAspLysLeuLysAlaGluArgGluArgTyrHisTyrIleThrIleAspIleAlaLeuTrpL
```

FIGURE 3C

```
                ScaI
                 |
1105  AGTTGAGACTACCAAGTACTATTGTACTGTCATTGATGCTCCTGGTCATAGGATTCATCAAGAACA  1173
      ysPheGluThrThrLysTyrTyrCysThrValIleAspAlaProGlyHisArgAspPheIleLysAsnM
                                                                      1123

KpnI
            |
1174  TGATTACTGGTACCTCTCAAGCTGTCTGCTCTGATTATCGACTCCACGACTGGTGTTTGAAG  1242
      etIleThrGlyThrSerGlnAlaAspCysAlaValLeuIleIleAspSerThrThrGlyGlyPheGluA
                 1187

1243  CTGGTATCTCTAAGGATGGACAGACTCGTGAACATGGTTGCTTGCTTTCACACTTGGTGTTAGGCAAA  1311
      laGlyIleSerLysAspGlyGlnThrArgGluHisAlaLeuLeuAlaPheThrLeuGlyValArgGlnM

1312  TGATTGTTGCTGCAACAAGTTTGCTCTTTCTTCTTCAAGTTTTAACTCACTCTAACACCCCCTTAACACC  1380
      etIleValAlaAlaThrSerLeuLeuPheLeuLeuGlnValLeuThrHisSerAsnThrProLeuThrPro
                 ETIleCysCysCysAsnLys

1381  CCAATGCCTAAAACGGAGATGGACCTGACTCGATACCATGTAAAGATATGACATCTGGACCTAACTCA  1449
```

FIGURE 3D

```
1450  ACCCAAAAGCTAACTCATGAGCTACGAGGGGAGGATTGTTCAAGTCCATTCCCAATGATTAGCTAACT  1518
1519  CATGAGGGTAGCTCATGAGGGTGGATTGTCCAAGTTCATTCTCTAATGATTGGGACTTAACCAACTC  1587
1588  AAACAGATGTTACCTGAAGAATGCTGCTTCATGTTTTGCTAATGTGTTTTTACTCCTTGTGTAGATGGA  1656
                                                                    METAs
1657  TGCTACCACCACCTAAGTACTCCAAGGCTAGTTATGATGAAATTGTGAAGGAAGTGTCTCTTACCTTAA  1725
      pAlaThrThrProLysTyrSerLysAlaArgTyrAspGluIleValLysGluValSerSerTyrLeuLy
                            ScaI
                            ——
                            1674
1726  GAAGGTTGGTTACAACCCTGACAAGATCCCATTTGTGCCGATTTCTGGTTTCGAAGGAGATAAATATGAT  1794
      sLysValGlyTyrAsnProAspLysIleProPheValProIleSerGlyPheGluGlyAspAsnMETIl
1795  TGAGAGATCAACTAACCTGGAGCTCCAACCCTCTTGAGGCTCTTGACCAGCTTAATGA  1863
      eGluArgSerThrAsnLeuAspTrpTyrLysGlyProThrLeuLeuGluAlaLeuAspGlnLeuAsnGl
1864  GCCTAAGAGGCCCTCGGACAAACCCTTGCGTCTTCCACTTCAGGATGTCTATAAGATTGGGGGATTGG  1932
      uProLysArgProSerAspLysProLeuArgLeuGlnAspValTyrLysIleGlyGlyIleGl
```

FIGURE 3E

```
1933 GACTGTTCCTGTTGGTCTGTTGAGACTGGTGTGATTAAGCCTGGTGTGTGACTTTTGGTCCTAC 2001
     yThrValProValGlyArgValGluThrGlyValIleLysProGlyMETValValThrPheGlyProTh

NsiI
                                              |

2002 TGGTCTGACTACTGAAGTTAAGTCTGTTGAGATGCATCATGAAGCTCTTCAAGAGGCACTGCCTGGTGA 2070
     rGlyLeuThrThrGluValLysSerValGluMETHisHisGluAlaLeuGlnGluAlaLeuProGlyAs
                                          2038

2071 TAATGTTGGTTTTAACGTCAAGAATGTTGCGGTTAAGGATCTTAAACGTGGATTGTGCTTCCAACTC 2139
     pAsnValGlyPheAsnValLysAsnValAlaValLysAspLeuLysArgGlyPheValAlaSerAsnSe

2140 CAAGGAGGATGACCCAGCTAAGGGGGCTAGCTTCACCGCTCAGGTCATCATCATGAACATCCAGGACA 2208
     rLysAspAspProAlaLysGlyAlaAlaSerPheThrAlaGlnValIleIleMETAsnHisProGlyGl
```

FIGURE 3F

```
                                                                                    BglII
                                                                                      |
2209 GATTGGAAATGGATATGCTCCAGTGCTGCTGGACTGTGTCAAGTTGCTGAGAT 2277
     nIleGlyAsnGlyTyrAlaProValLeuAspCysHisIleAlaValLysPheAlaGluIl
                                                                       2275

XhoI
                              AvaI
                                |
2278 CTTGACTAAGATTGACAGGCGTTCTGGTAAGGAACTGAGAAGGAGCCTAAGTTCTTGAAGAACGGTGA 2346
     eLeuThrLysIleAspArgArgSerGlyLysGluLeuGluLysGluLeuLysPheLeuLysAsnGlyAs
                                                       2313

NcoI
                       |
2347 TGCTGGTATGGTTAAGATGATTCCCACCAAGCCCATGGTTGTTGAGACATTCCCGAGTACCCACCATT 2415
     pAlaGlyMETValLysMETIleProThrLysProMETValValGluThrPheSerGluTyrProProLe
                                                 2380

HincII
                                                                   |
2416 GGGACGTTTGCTGTGAGGACATGCGTCAAACTGTTGCTGTTGGTGTTATCAAGAATGTTGACAAGAA 2484
     uGlyArgPheAlaValArgAspMETArgGlnThrValAlaValGlyValIleLysAsnValAspLysLy
                                                                 2474
```

FIGURE 3G

2485 GGACCCATCTGGAGCCAAGGTCACCAAGGCTGCTCAGAAGAAAAAA TGA ATAGTGCAGTTCAACTCTGG 2553
     sAspProSerGlyAlaLysValThrLysAlaAlaGlnLysLysLys

2554 AGTTACCAGAGATATCAGTATCTACTATATAAAGTGTGTTATGAAACTTGCTATACTTACTCTTCC 2622
                EcoRV
                 |
                2567

2623 TGCTCATGTTCAGTCTTTTATGTGTTGTTTGGTTCTTGTTTCTGCCCTGTATGTCAGGTATCCTTTC 2691

2692 CCAGAACTGGGTGCTCGACAGAGTCATTGGTTTATCTTTTGAGG 2760
                              HindIII
                                |
                               2790

2761 TGCCTAGGTTCATCCAAGACAGGCTAAGAAGCTTGTTATTTATGTTTCTTATAACACGTAAATCGTA 2829

FIGURE 3H

2830 CTTTTCTGTGTTTTGTGCTGATAATCTTCTATTGCATCATCTATCCTGTTTTCCCTTGACATAGTTTG 2898

2899 GATAACTTGTTGAAGTCTCTGGATGAGGTTGTGGGCAACTCAACTATTCATTGAATACTTGCTACCT 2967

2968 CCCGTCAATATGAATTAACTCCGCCCACCAAGCTTAGACAAATGAGAAAGATTACCTAGCA 3036
                       BclI                    HindIII
                        |                         |
                       3005
                       3041

3037 TTATGATCATCACTAATAATCAAGGTCACTTAGGAACACAACATCTCTCTGATAAATACTATAAGACAA 3105

FIGURE 31

3106 ATTGAGGTTCCCATTGAATCAGGCAACAACCTAATAGGTAGCTACAAATACACAATTTAGGGTTCTG 317

3175 GAGGGGGACAGTCATCAGGTGCATGTCGTATACTCTAAAAGTGGTAAGTGGTAAGTAGTGCATACTTAGAGAGCCG 3243
                            Acc
                             |
                            3204

3244 ATATGGGTACAGCAACATTTGGACAGTCCGAGCAACATAAATTTACTCCCACTATCCCACTACTGTATA 3312

3313 AAAGCTATGAACCAAGAAACTGAACCAAAAGTTGCTAGTAATATAGTATTTATCTTGAATTC 3374
                                                        EcoRI
                                                          |
                                                         3370

FIGURE 3J

EF-GENOMIC     Linear     LENGTH = 4565

```
                                  DdeI                                          Sau3AI
                                   |                                              |
  1 ATGTGTGTTATATTAGGTCTTAGACGAAATTCATTCCCAAAAGGTAGATCAAATAGAGGAGGATTGTCC
                                   20                                            47                        69

TaqI
                                                        ClaI
                                                         |
                                                        105
                                                        105
 70 AAATATTATAAGAAGTCACTTCATTCATTAATCATCGATGTAGAATTTTTTCATTCTTTAACACCCTA     138

DdeI
                     |
                    154
139 TATCACGTCAAGTGCTTAGCATGTTGTGTATGGACAATTTTGACTTTAAGAGCCCCAACATTGCACACT     207
```

FIGURE 4R

```
208 TTACCTTCTTTTTTTGAAAAATTAACAACAATTTTTTTCCTACTTATTCAATACCTTGTTCAAT 276

DdeI     RsaI
               |        |
277 AATAAAGAACTAAGATAGTACGAAGAGAATTTATTATTTTGTCTAGCAATTAATAATAAATAATA 345
                   287     296

346 ATGTAACAAACATTCTATGAAATATATATTATTCTCTTTTCCAAGCAAAATTAAAAATGATAACCAA 414

DraI                                        AluI
     |                                           |
415 CAATTAAAAACTTATCCTACAATATAAGTTCATAAAAAAATAATTAGCTTGCCAATTGGCTTAACCAG 483
         421                                            463

484 ATTGCAATTATATATATATATATATATAATAATAAT?·TAATATATAATAAATATTTTAACTTTTTC 552
```

FIGURE 4B

```
                                   DraI
                                    |
553 TCAACAAAAAAATACTGTTGCTGCTTTCAGTTTAAATCAGTTTAAGAGTTTACGAAAATTAATTA 621
                                   587

DraI
        |
622 TTTAAGTAAGTATATTTTCAATAACAATGCCAAAACCTCTAATATTCTTAATTAACAATTGCCAA 690
    625

691 GTGATTTTTAGTTAGTTTGCTATTACTATTGTTGTTATCCTTACTACTAGCATTATTACTATTAATTAA 759
```

FIGURE 4C

```
760  TTATTATTATTATCATCACTATCATTATTAGTAAAAGGTTTTTTTATGTTTGTATCTTTTAATTTAAT  828

DraI
                 |
829  ATTAAATTAAATACATTTACATTTATTTGCAATATTTAAAAATGATTAGTTGTCAAATAGTAGAGT  897
                                     868

TaqI
                                                                SalI
                                                                HincII
                                                                AluI AccI
                                                                 | |||
898  TCATTTAAAATTCTTCAGCCATATAGTTCTATTTTAAGCTAGTCGACTTTTTTTTCTTACTGAAAAT  966
          |                                           937 942
         DraI                                           940
          904                                            941
                                                          942

967  TAATATTTTTTTCTTTTGAAATACTAATAACATCTAAATTAACAATTGCCAAAGTGATTTTTAATTAG  1035

AluI
      |
1036 CTTGCTGGCTAATCACAATACAAATTACTCTCCTTACTATATAAGTAAATTTTATTGCTATATTGT  1104
      1036
```

FIGURE 4D

1450 GTTTTATTATAATATGTATAAATATAAAAAATAGATATTCCATAACATATATTATAAAAAATGTAAGGGGCA 1518

1519 TTTACGTAAATAGATAGACTTAAAGAGGCACCGAGTGAACCCTAATTCTCATCGTTGAGACTATAAAA 1587

PvuII
                                    DdeI AluI
         START OF cDNA                    |  |
                                   1641 1645

1588 TGCCCATTATCCCATAGTCTCTTCATTACTTTGCTGTGATTTCTCCTCAGCTGTGCCGCATA 1656

TaqI
   DdeI                                           HinfI
   |                                             | |

1657 TCGCCTAATTTTCTTCTCTAAGgttcatcatcatctcttcaccaattcttaatctcgattcaattttta 1725
               1676                                  1711 1713

Sau3AI
|

1726 tgtttgatctgtattgttctgtcactacatgtgttttcagttgttttactagatgattcactgtc 1794
 1731

FIGURE 4F

```
           Sau3AI
             |
1795 ttcctgttagatcatacatatattgaaaatgttttgattgactttttgtattgtgatatctgttat 1863

Sau3AI                    AluI
                           |                        |
1864 tgtttgatagttgttcagtattacacagccgatctgtgttatgagcttggtcataactatttctgt 1932

Sau3AI                                  NdeI
     BglII                                    |
1933 atgtaaatacagatctgttaatgtttgtaatcaattttcatatgcactgttgatattgttctctcc 2001

HinfI
                            |
2002 tgtccctgttatatgttgatatgttcggttttgtgtaactgaactaaacactagtccTaatgtttt 2070

HindIII
                                                          AluI
                                                           ||
2071 ttttactattaagatttatataatgGatagattTgttgagttccTagtctctgaagaggttaagct 2139
                                                             2138
                                                             2136

FIGURE 4G
```

2140 tgctgtgtagttgttaccagttgagttgcaatactaaaaatcaattcattactgatattttgctgtt 2208

2209 taggtttttgacgaagtacttaattgcttattgaactaaaaacgtagtcctgaattcattgcaagt 2277
                        ScaI                                    EcoRI
                        RsaI
                        2226
                        2226                                    2264

2278 gtgaaagctatagttcattgttttgtgttgcaattcctgaaaatcaattggtcaagctataatgattt 2346
         AluI                                                    AluI
         2285                                                    2334

2347 acttttctgtttaaatgttgaatgcgctgaatttatgaatgggttgcatggttttgaaatatgttg 2415
                      DraI      HhaI
                      2361      2375

2416 ttgtgtgttgtgtaaatgcagTTTCTTAGTGTCTCAAGATGGGTAAAGAGAAGATTCACATCAGCATTG 2484
                         DdeI                              HinfI
                         2441                              2469
                         METGlyLysGluLysIleHisIleSerIleV

FIGURE 4H

```
                          TaqI
                          SalI
              HinfI       HincII                              HindIII
              HincII      AccI                       Sau3AI   AluI
              |           |||                        |        |
2485 TGGTCATTGGTCATGTTGACTCTGGAAAGTCGACTACCACTGGTCACTGACTCTACAAGCTTGGTGGTA 2553
     alValIleGlyHisValAspSerGlyLysSerThrThrThrGlyHisLeuIleTyrLysLeuGlyIyI
                     2499   2513                          2534       2542
                            2514                                  2544
                        2503 2515
                            2515

DdeI
                                 TaqI         AluI
                                 |            |
2554 TTGACAAGCGTGTTATTGAGAGGTTCGAGAAGGAAGAGCTGCTGAGATGAACAAGAGGTCATTCAAGTATG 2622
     leAspLysArgValIleGluArgPheGluLysGluAlaAlaGluMETAsnLysArgSerPheLysTyrA
                               2579               2590
                                                    2594

BstNI
     |
2623 CCTGGGTGCTTGACAAACTTAAGGCAGAACGTGAGCGTGGTATCACCATTGATATTGCTTTGTGGAAGT 2691
     laTrpValLeuAspLysLeuLysAlaGluArgGlyIleThrIleAspIleAlaLeuTrpLysP
     2625

FIGURE 41
```

```
2968  atgctaattctgttattttttgtagATGGATGCTACCACCCCAAGTACTCCAAGGCTAGGTATGA  3036
                              METAspAlaThrThrProLysTyrSerLysAlaArgTyrAs
                                                                    3018
                                         ScaI
                                         RsaI
                                          -

3037  TGAAATCGTGAAGGAAGTTTCTTCCTACCTCAAGAAGGTTGGTTACAACCCTGACAAAATCCCCTTTGT  3105
      pGluIleValLysGluValSerSerTyrLeuLysLysValGlyTyrAsnProAspLysIleProPheVa

3106  TCCAATCTCTGGTTTGAAGGAGACAACATGATTGAGAGGTCTACCAACCTGACTGGTACAAGGGACC  3174
      lProIleSerGlyPheGluGlyAspAsnMETIleGluArgSerThrAsnLeuAspTrpTyrLysGlyPr
                                      3147           3157       3165  3171
                          AccI        TaqI        RsaI    AvaII
                           -           -           -      -

HaeIII
                                -

3175  AACCCTCCTTGAGGCTCTTGACCAGATTAACGAGCCATCAGAGAGCCAAGAGCCCAAGACAAACCCCTCCGTCTTCC  3243
      oThrLeuLeuGluAlaLeuAspGlnIleAsnGluProSerAspLysProLeuArgLeuPr
                                                                3218
```

FIGURE 4K

```
                                                                Sau3AI
                                                                BclI
                                                                  |
3244 ACTTCAGGATGTTACAAGATTGGTGGTATTGGAACTGTCCCTGTTGGTCGCGTTGAGACTGGTGTGAT 3312
     oLeuGlnAspValTyrLysIleGlyGlyIleGlyThrValProValGlyArgValGluThrGlyValIl
                                                                      3310

BstNI           HaeIII
            |               |
3313 CAAGCCTGGTATGGTTGTGACCTTTGCCCTACTGGTTGACAACTGAAGTCAAGTCTGTTGAGATGCA 3381
     eLysProGlyMETValValThrPheGlyProThrGlyLeuThrThrGluValLysSerValGluMETHi
                  3319

AluI BstNI                                      BstNI
              |   |                                           |
3382 CCACGAAGCTCTCCAGGAGGCACTCCCTGGTGACAATGTTGGGTTCAATGTTAAGAATGTTGCTGTTAA 3450
     sHisGluAlaLeuGlnGlnLeuProGlyAspAsnValGlyPheAsnValLysAsnValAlaValLy
                   3390 3396                                  3409

Sau3AI                                               AluI
       |                                                    |
3451 GGATCTTAAGCGTGGTTATGTTGCCTCAAACTCCAAGGATGACCCAGCCAAGGGGGCAGCCAGCTTCAC 3519
     sAspLeuLysArgGlyTyrValAlaSerAsnSerLysAspAspProAlaLysGlyAlaAlaSerPheTh
        3452                                                   3514

FIGURE 4L
```

```
                    BstNI
                    HaeIII
                    BalI
    BstNI           |
    |
3520 TGCCCAGGTCATCATCATGAACCATCCTGGCCAGATTGGAAATGGATATGCTCCAGTGCTTGATTGTCA 3588
     rAlaGlnValIleIleMETAsnHisProGlyGlnIleGlyAsnGlyTyrAlaProValLeuAspCysHi
     3525                                3547 3550
                                              3550
```

```
                    Sau3AI
                    DdeI
                    BglII
                    |
3589 CACTTCCCACATTGCTGTGTCAAGTTTGCTGAGATCTTGACCAAGATTGACAGGCGTTCAGGTAAGGAACT 3657
     sThrSerHisIleAlaValLysPheAlaGluIleLeuThrLysIleAspArgArgSerGlyLysGluLe
                                        3616
                                        3619
                                        3619
```

```
            DdeI                    HinfI        NcoI
            |                       |            |
3658 TGAGAAGGAGCCTAAGTTCTTGAAGAACGGTGATGCTGGTATGGTTAAGATGATTCCACCAAGCCCAT 3726
     uGluLysGluProLysPheLeuLysAsnGlyAspAlaGlyMETValLysMETIleProThrLysProME
            3670                    3710        3724
```

FIGURE 4M

```
3727 GGTTGTTGAGACCTTTGCTGATACCCTCCATTGGGTCGTTTGCTGTGAGGGACATGAGGCAGAGACTGT 3795
     TValValGluThrPheAlaGluTyrProProLeuGlyArgPheAlaValArgAspMETArgGlnThrVa

HincII    AvaII           BstEII
                           |         |               |
3796 TGCTGTTGGTGTTGTCAAGAATGTTGACAAGAGGACCCAACTGGTGCCAAGGCTGACCAAGGCTGCCCA 3864
     lAlaValGlyValValLysAsnValAspLysLysAspProThrGlyAlaAlaLysValThrLysAlaAlaGl
                              3818                 3830          3848

TaqI              TaqI
                                                     |                 |
3865 GAAGAAGGGGAAGTGAACTGTGCAGTGTGATGCTATTATTACATCGAGTGTG 3933
     nLysLysGlyLys                3906                3926

XbaI  HinfI
      |     |
3934 CTATCTAGACTCTGTTTTATTTAATTCTGCTTAGTTTGGTCTTTGAGTTGTGTATTAGTTGTGTGGTTC 4002
         3938
     3942

FIGURE 4N
```

PLANT ELONGATION FACTOR PROMOTERS, CODING SEQUENCES AND USES

CROSS-REFERENCE TO RELATED APPLICATIONS

This is a continuation of application Ser. No. 07/393,366, filed Aug. 18, 1989, now abandoned, which is a continuation-in-part of U.S. application Ser. No. 07/335,133, filed Apr. 7, 1989, now abandoned which is a continuation-in-part of U.S. application Ser. No. 07/234,187, filed Aug. 18, 1988, now abandoned which disclosures are hereby incorporated by reference.

INTRODUCTION

1. Technical Field

The field of this invention relates to compositions and methods for modification of plant phenotype by preferential transcription of a gene of interest in specific tissue(s).

2. Background

With an increasing population, there is a continual demand for an increasing supply of food staples. In addition, in the wealthy societies, there is an expanding interest in food variety and improvement in organoleptic properties. Much of the revolution in agriculture in the increase of land utilization has been a result of the use of fertilizers. However, the use of fertilizers is a mixed blessing, in that the soil becomes ultimately less productive and the ground water becomes contaminated, resulting in eutrophy in various bodies of water.

With the ability to introduce DNA into plants, there is the potential to modify the phenotype of the plant. Various modifications have already been made and continue to be made. One modification of interest has been herbicide resistance. By providing for the crop being herbicide resistant, ore can provide for clear discrimination between the crop and weeds. Thus, the weeds may be destroyed, so that there is no diversion of nutrient and water to unproductive plants.

Initially, constitutive production of herbicide resistance was introduced into plants, so that there was a substantially constant amount of the herbicide resistant product being produced throughout the plant, regardless of the utility of such capability in various tissues. A further improvement resulted in the modification in the herbicide resistant gene with a leader sequence which allowed for transport of the gene into the chloroplast where the herbicide target was in the chloroplast. Since some herbicides inhibit enzymes present in the chloroplast providing for a herbicide-resistant enzyme in the chloroplast would maintain the enzyme function at the natural site where it is utilized. Other improvements have involved introduction of insect resistance, where an insecticidal protein existing naturally in bacterial organisms is introduced into plants for expression and resistance of the plant to insects.

In many instances, there is a particular interest in protecting rapidly dividing cells or rapidly growing tissue against stress or other detrimental factors. For example, the site of action of various herbicides is rapidly dividing cells. Insects frequently target young tender tissue for attack resulting in injury at this site. Certain plant diseases are particularly severe with young rapidly dividing cells. Also, the tender new tissue is most sensitive to stresses such as frost, so that enhanced production of products which protect against frost or inhibition of endogenous products which enhance the sensitivity to frost is of primary interest in such tissue.

There is, therefore, substantial interest in being able to target particular products to rapidly dividing cells in young tissue. In some instances, the protein which is produced may be deleterious to other tissue at elevated levels, so that one wishes to restrict expression to the rapidly dividing cells. In other situations, the product will have no utility at other sites, so that the energy of the plant is wasted, reducing growth efficiency. Toward this end, it is important to identify genes and their promoters which will allow for expression in selected tissue(s) at a desired high level, while providing for low- or no-level of expression in other tissue.

Relevant Literature

Genes encoding elongation factor-1α from several species have been cloned and sequenced. These include yeast (Nagata, et al., *EMBO J.* (1984) 3:1825-1830); the brine shrimp *Artemia salina;* (van Hemert, et al., *FEBS Lett.* (1983) 157:295-299; the fungus *Mucor racemosus* (Linz, et al., *J. Biol. Chem.* (1986) 261:15022-15029); and man (Brands, et al., *Eur. J. Biochem.* (1986) 155:167-171). For a review of elongation factor-1α (EF-1α) protein, see Ejiri, *Methods in Enzymology* (1986), 118:140-153.

BRIEF DESCRIPTION OF THE DRAWINGS

FIG. 1 shows the sequence of LeEF-1.

FIG. 2 shows amino acid comparisons between tomato and other EF-1α proteins. 1=*L. esculentum* (tomato; LeEF-1 this paper); 2=*A. salina* (brine shrimp) (van Hemert et al., 1984); 3=*H. sapien* (man) (Brands et al., 1986); 4=*M. racemosus* (a dimorphic fungus) (Linz et al., 1985); 5=*S. cerevisiae* (yeast) (Nagata et al., 1984). Boxes indicate residues which are homologous tomato EF-1α.

FIG. 3 shows the sequence of the EF-1α genomic clone, 61-1 from tomato.

SUMMARY OF THE INVENTION

Figure 4E:
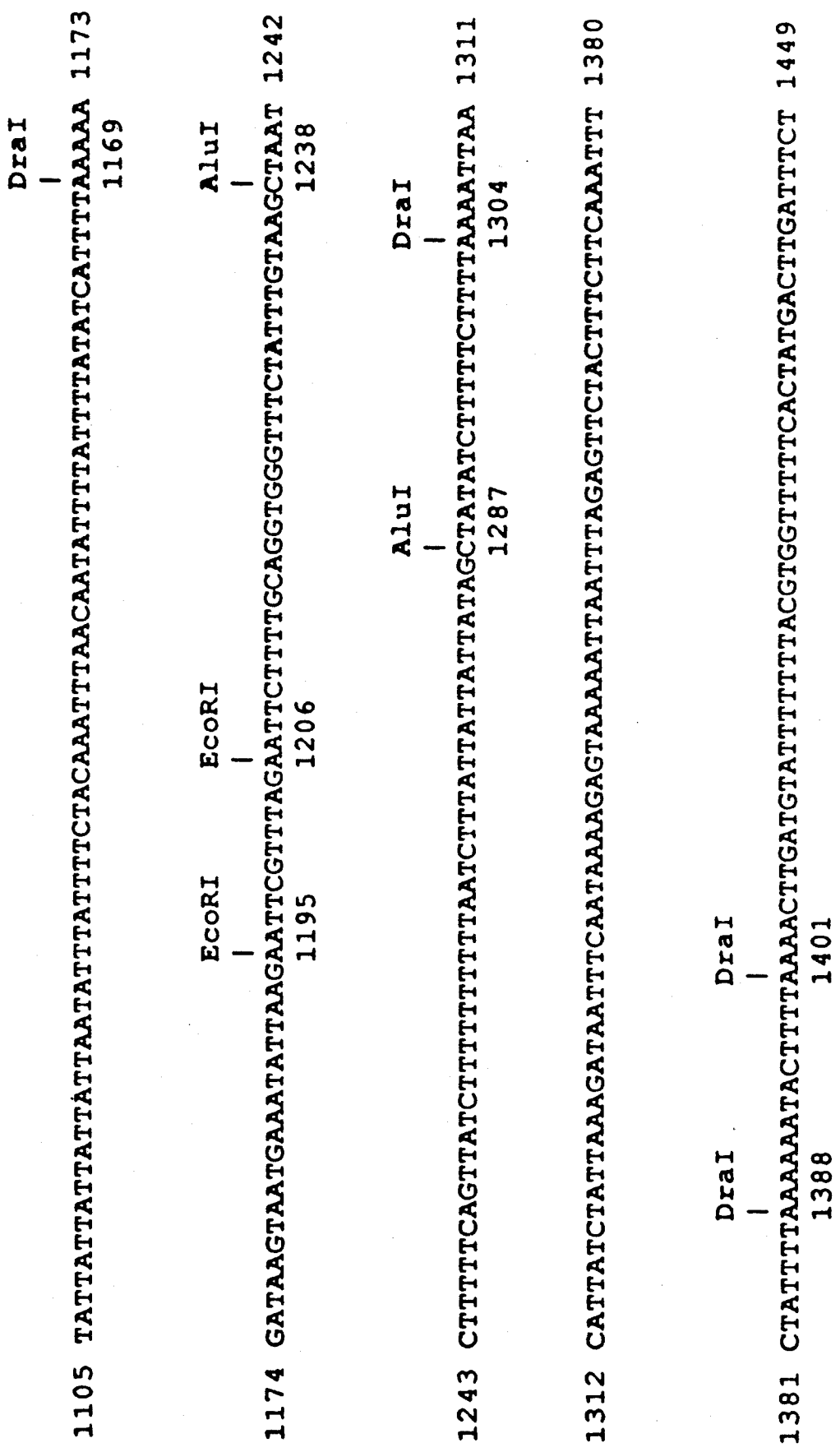
FIG. 4 shows the sequence of the EF-1α genomic clone, clone A, also referred to as LeEF-A.

Novel DNA transcription constructs, together with methods for their preparation and use, are provided for modifying the phenotype of plant cells and tissues. Also provided is a DNA sequence for preparation of the transcription constructs. When transformed into a plant cell, the transcription constructs provide for a transcription pattern of a gene of interest associated with that of elongation factor-1α (EF-1α). The DNA comprises the 5' non-coding regions associated with the plant EF-1α to and including the entire coding region for the plant EF-1α and also the 3' non-coding region. DNA transcription constructs are prepared which include the transcriptional and translational regulatory region of EF-1α and a gene of interest other than the EF-1α gene under the regulatory control of the regulatory region and a termination region functional in a plant cell. The transcriptional construct can be used to insert any of a variety of endogenous or exogenous genes into a plant cell for high level production of transcription products, as well as translation products associated with varying the phenotype of specific plant cells and tissue.

DESCRIPTION OF THE SPECIFIC EMBODIMENTS

Novel DNA sequences, constructs employing such sequences, plant cells containing such constructs, and plants containing such constructs, are provided, where the sequences are associated with elongation factor-1α (EF-1α). In addition, a method is described for identifying the genes for EF-1α, since it is found that EF-1α is a multi-gene family in plants. Plant EF-1α is characterized by having a mRNA of about 1.5–2 kb, a molecular weight in the range of about 45–55 kd, and a PI of about 8.5 to 9.5. The polypeptides encoded by plant EF-1αs have substantial homology with the polypeptides encoded by EF-1αs from a wide variety of species.

The transcriptional initiation regulatory region is found to provide regulation, where enhanced levels of EF-1α are expressed in rapidly dividing tissue, while lower levels are expressed in mature cells and tissue. An EF-1α gene isolated may be used to regulate expression in transgenic plants. For example, a promoter derived from an EF-1α gene has been shown to direct expression of a foreign gene in tomato and in tobacco plants.

Significant levels of plant EF-1α mRNA are found in substantially all tissues, e.g. young leaf, young root, mature leaf, mature root, green fruit, turning fruit and ripe fruit, generally ranging in values from 0.1 to 1.0%, as evidenced with the experience in tomato. Levels of EF-1α mRNA decrease in both the leaves and roots as they mature, and in fruit as it ripens.

The plant EF-1α sequence may be isolated from any convenient plant. When used in a construct, the EF-1α sequence may be endogenous to the target host or exogenous to the target host. Plants from which EF-1α may be isolated include fruit, vegetables, oil seeds, fiber sources, grasses, trees, flowers, grain, ornamentals and the like. Particular plants of interest include tomato, pea, tobacco, maize, soybean, Brassica, cotton, wheat, alfalfa, turf grass, and the like.

The plant EF-1α gene may be isolated by various techniques. These include isolating mRNA from a host organism which codes for the EF-1α, reverse transcribing the mRNA, and using the resulting single-stranded (ss) DNA as a template to prepare double-stranded (ds) DNA and the ds DNA isolated. Among multi-gene families it is desirable to find the transcriptional initiation regulatory region which provides a high level of transcription. Thus, the transcriptional initiation regulatory region should provide for at least about 10% of the total EF-1α mRNA, preferably at least about 20%, and more preferably at least about 30%. This can be determined by employing two probes, one probe which is conserved and binds to all EF-1α mRNA, and the other probe being in a polymorphic region of the EF-1α locus which binds uniquely to the EF-1α gene being assayed.

The sequences provided in the experimental section may be used to identify plant EF-1α genes from plant sources other than tomato. Particularly, by identifying sequences of the subject plant associated with the EF-1α gene, which sequences are conserved in species other than plants, these conserved sequences may be used as probes for hybridization to cDNA obtained from a number of different plant sources. Usually, the sequence will have at least about 60%, preferably at least about 70%, identity of base pairs, excluding any deletions which may be present. Thus cDNA libraries may be prepared from the plant source of interest, and the probes used to identify cDNA sequences for EF-1α. Conveniently, the target cDNA may be cloned in a virus, so that hybridizing phage may be plaque-purified. The identified cDNA's may be further sub-cloned and the sub-clone sequence analyzed and used for production of probes. The probes are then used to identify cDNA EF-1α sequences in a cDNA library. The cDNA is used to identify genomic sequences in a plant genomic library of the appropriate plant species and the positive clones analyzed by restriction enzyme digestion. The level of transcription may then be determined in a variety of plant tissues to demonstrate the pattern of transcription in the plant. In this manner, one or more sequences may be identified providing both the coding region, as well as the transcriptional regulatory elements of the gene.

The probes can be considerably shorter than the entire sequence, but should be at least about 10, preferably at least about 15, more preferably at least about 20 nucleotides in length. Longer oligonucleotides are also useful, up to the full length of the gene encoding the polypeptide of interest. Both DNA and RNA probes can be used.

In use, the probes are typically labeled in a detectable manner (for example with $^{32}P$-labelled or biotinylated nucleotides) and are incubated with single-stranded DNA or RNA from the organism in which a gene is being sought. Hybridization is detected by means of the label after single-stranded and double-stranded (hybridized) DNA or DNA/RNA have been separated, typically using nitrocellulose paper. Hybridization techniques suitable for use with oligonucleotides are well known to those skilled in the art.

Although probes are normally used with a detectable label that allows for easy identification, unlabeled oligonucleotides are also useful, both as precursors of labeled probes and for use in methods that provide for direct detection of DNA or DNA/RNA. Accordingly, the term "oligonucleotide" refers to both labeled and unlabeled forms.

Once the 5'- and 3'-non-coding regions of the EF-1α gene have been identified, they may be manipulated in accordance with conventional ways. Where a convenient restriction site is present downstream from the ATG initiation codon, it may be useful to cut at that site and insert a DNA sequence of interest for transcription under the regulatory control of the EF-1α regulatory elements. Where the DNA sequence of interest is a structural gene, the sequence of interest will be inserted so as to be in reading frame with the upstream codons and the initiation methionine. Where the DNA is to be used as an anti-sense sequence, it need not be in reading frame with the upstream codons.

Usually, not more than 20 codons at the 5'-end of the EF-1α gene will be retained. Preferably, the sequence of interest will not be fused to the 5'-region of the EF-1α gene but rather may be joined to the transcriptional initiation regulatory region of EF-1α in a variety of ways. One can cleave internal to the EF-1α gene and resect using Bal31. By blunt-end ligation of the gene of interest to the various EF-1α fragments, one can screen for expression of the gene of interest indicating that a functional transcription initiation region has been retained. To join a sequence, one may use the polymerase chain reaction where an oligonucleotide containing the sequence of interest hybridizes at one end with the terminal sequence of the EF-1α transcriptional initiation regulatory region and/or 5'-untranslated region. By providing for replication using the polymerase chain reaction, dsDNA may be prepared for insertion into a vector which will have the EF-1α transcriptional initiation regulatory region properly joined to all of, or the 5'-proximal portion of, the sequence of interest.

Conveniently, one may identify a convenient restriction site in the 5'-untranslated region of EF-1α and in the 5' region of the gene of interest and employ an adapter which will join the two sequences and restore the lost sequences from the 5'-untranslated region and the 5' region of the gene of interest. Alternatively, one may introduce a polylinker immediately downstream from the 5'-untranslated region, for insertion of the DNA sequence of interest.

The 5'-non-coding region which will be employed for joining to the sequence of interest will usually be at least about 100 bp, and not more than about 10 kbp, frequently being less than about 2 kbp, and may include all or a portion of an intron (including the splice sites). The 5'-non-coding region which is employed will be proximal to (usually within 20 bp) or abut the initiation codon. Therefore, by employing sequence analysis, one can identify the initiation codon of the EF-1α gene and isolate the upstream region in accordance with conventional ways. Where a particular cloned fragment in a genomic library does not have the desired size, the library may be further screened by walking the 5'-non-coding region until a fragment of the desired length is obtained. The 5'-non-coding region may then be cloned and sequenced and may then be used for further manipulation. As already indicated, in some instances, at least a fragment of the 5'-coding region may be retained.

The EF-1α transcriptional initiation regulatory region (promoter) may be inserted into a vector for preparing a construct for transcription and optionally translation. The 3' terminus of the EF-1α promoter may be joined to a sequence of interest, which may be a structural gene or coding or noncoding sequence where anti-sense may be desired. A wide variety of genes are of interest for transcription and optionally translation in rapidly dividing cells. For example, tender shoots and tissue are particularly sensitive to stress. Stress may take the form of toxins, such as pesticides, or herbicides, temperature changes such as heat or cold, including ice formation, osmotic pressure as a result of salinity, drought, and the like. Stress may include attack by various organisms or susceptibility to disease, as evidenced by insects, nematodes, aphids, caterpillars, fungi, and the like. Growth may be modulated, either increased or decreased, depending upon the particular need. Anti-sense sequences may be used to reduce growth, for example, altering the auxin/cytokinin ratio may be used to alter growth rate and/or morphology. By enhancing or diminishing the expression of an enzyme in the metabolic pathway for the hormone, the ratio may be modulated.

For resistance to toxins, various genes may be employed which may be the target of the toxin, where a mutated gene is employed which is less sensitive or insensitive to the toxin. Alternatively, one can enhance the amount of the target protein, so as to reduce the sensitivity of the plant cells to the toxin. For example, 5-enolpyruvyl-2-phosphoshikimate synthase is the target for glyphosate (aroA gene). By providing for an aroA gene which is less sensitive to the herbicide and/or enhancing the level of the enzyme present in the cell, particularly in the chloroplast, herbicide-resistance may be achieved. Alternatively, a gene which provides for detoxification may be employed, such as a nitrilase which hydrolyzes the nitrile group of bromoxynil. Additional examples are the herbicide phosphinothricin which may be detoxified by phosphinothricin acetyltransferase from *Streptomyces hygroscopicus* (bargene) and acetolactate synthase which may be mutated to be resistant to various sulfanyl-urea herbicides.

For insects or nematodes, there are naturally occurring toxins for the pest which may be provided as a gene for expression in the plant cells. For example a number of strains of *Bacillus thuringiensis* have relatively broad spectrum toxicity to a number of different insects as a result of expression of a protein toxin. By providing for expression of the protein toxin in plant cells, particularly among rapidly dividing cells, these cells will be protected from attack by such insects. Protection may also be provided against nematodes and fungus, and root worm, e.g. corn root worms.

For providing resistance to frost or heat, various genes may be employed, such as heat shock proteins, winter flounder antifreeze protein, etc. For stress tolerance such as salinity, Osm genes may be employed, such as genes associated with overproduction of proline. Additionally, stress tolerance may be provided by genes for superoxide dismutase.

The auxin/cytokinin ratio may be modified by modulating genes on the metabolic pathway to protect growing cells or to change growth rate. Other DNA sequences of interest in this regard include antisense EF-1α which may be used to modulate expression of EF-1α.

The EF-1α promoter, being a strong promoter, may be used in place of other strong promoters conventionally employed, such as the 35S cauliflower mosaic virus promoter. The subject promoters may also find use for a specific selectable marker where the target for transformation and regeneration is meristematic tissue e.g., for use with particle bombardment in cotton, soybean, etc.

Depending upon the sequence of interest, the purpose of the transformation and the particular host, other sequences may be included which provide for specific functions. In some instances, it may be desirable to provide for translocation of the expression product from the cytoplasm to an organelle or for secretion. In this instance, various transit peptides may be employed for translocating the gene of interest to an organelle, such as the chloroplast or mitochondrion, or to secrete the protein into the extracellular space or to the cell surface. Various transit peptides have been employed, such as the transit peptide of the small subunit of the RUBISCO gene, plant EPSP synthase, acyl carrier protein, and the like.

In addition to the promoter and the structural gene, there will be a termination region, which may be the EF-1α termination region or any other convenient termination region. A wide variety of termination regions have been employed, such as termination regions from opine genes, various plant genes, and the like. The particular termination region will usually not be critical to this invention and any convenient region may be employed.

The promoter, structural gene and transcriptional and translational termination region provide an expression construct which may be joined to a vector for cloning. At each stage of the preparation of the construct, the resulting product may be cloned and analyzed to insure that the desired product has been obtained. Cloning vectors conveniently will have one or more markers, which will allow for detection of transformants which contain the construct and marker. For the most part markers will provide for toxin resistance or impart prototrophy to an auxotrophic host. Toxin resistance for the most part will be antibiotic resistance, such as resistance to kanamycin and its analogs, e.g. G418, resistance to chloramphenicol, and the like. For the most part cloning will be performed in *E. coli*, so that a replication system functional in *E. coli* will be employed.

Once the expression construct has been prepared and analyzed to insure it has the proper sequence, it may then be used for introduction into a plant cell. Various techniques exist for introduction of DNA into plant cells. These techniques include *A. tumefaciens* mediated introduction, electroporation, protoplast fusion, injection, high velocity projectile introduction, and the like. The targets for introduction of the DNA may be tissue, particularly leaf tissue with *A. tumefaciens*, disseminated cells, protoplast, seeds, embryo, meristematic regions, cotyledons, hypocotyls, and the like.

With *A. tumefaciens* introduction, the construct will be further modified by having one or both T-DNA borders present, bordering the expression construct, particularly the right border. The construct may be introduced into *A. tumefaciens* carrying the vir genes, where the T-DNA bordered expression construct will be introduced into plant cells infected with *A. tumefaciens*. The plants which may be genetically modified include those plants described as the source of the EF-1α gene. Thus, of particular interest are those crops associated with food sources, such as grain, vegetables and fruits, oil seed, sugar sources, forage, and legumes.

Once the cells are transformed, transgenic cells may be selected by means of a marker associated with the expression construct. The expression construct will usually be joined with a marker which will allow for selection of transformed plant cells, as against those cells which are not transformed. The marker will usually provide resistance to an antibiotic, which antibiotic is toxic to plant cells at a moderate concentration.

After transformation, the plants cells may be grown in an appropriate medium. In the case of protoplasts the cell wall will be allowed to reform under appropriate osmotic conditions. In the case of seeds or embryos, an appropriate germination or callus initiation medium would be employed. For explants, an appropriate regeneration medium would be used.

The callus which results from cells may be introduced into a nutrient medium which provides for the formation of shoots and roots and the resulting plantlets planted and allowed to grow to seed. During the growth, tissue may be harvested and screened for the presence of expression of the expression construct. After growth, the seed may be collected and replanted, or prior to seed formation, the modified plant may be used for fertilizing a different strain or vice versa, so as to provide for a hybrid plant. One or more generations may then be grown to establish that the gene is inherited in Mendelian fashion.

Of particular interest is a gene associated with tomato, which has the amino acid and DNA sequence found in the Experimental section. The gene and its accompanying untranslated regions may be used in the anti-sense direction to inhibit expression in plant cells, so as to reduce growth. Thus, fragments of the gene and the untranslated regions of at least about 12 bp, usually at least about 20 bp may be employed to produce an mRNA which results in reduction in expression of the EF-1α gene.

The invention now being generally described, it will be more readily understood by reference to the following examples which are included for purposes of illustration only and are not intended to limit the invention unless so stated.

EXPERIMENTAL

Example I

EF-1α cDNA

A. Materials and Methods

1. Screening a Tomato cDNA Library for EF-1α Clones

A red, ripe tomato (*Lycopersicon esculentum* cv "Caligrande") cDNA library in λgt10 (Sheehy, et al., *Mol. Gen. Genet.* (1987) 208:30–36) was screened for EF-1α cDNAs. $1 \times 10^5$ recombinant plaques of the λgt10 library grown in *E. coli* strain C600 hfl A150 (Hoyt, et al., *Cell* (1982) 31:565–573) were transferred to GeneScreen Plus filters (New England Nuclear) denatured, and neutralized by a modification of the procedure of Benton and Davis, *Science* (1977) 196:180–182, as described in O'Neal et al., *Nucl. Acids Res.* (1987) 15:8661–8667). The probe used was isolated from pMUEF-1 which contains the *Mucor racemosa* EF-1α gene, TEF-1 (Linz, et al., *Mol. Cell. Biol.* (1986) 6:593–600. A 471 bp claI fragment from pMUEF1-2, which spans nucleotides 219 to 689 of TEF-1 (corresponding to amino acids 73 to 230) (Linz, et al., (1986) *Mol. Cell. Biol.*, 7:1925–1932) was isolated and nick-translated as previously described (Shewmaker, et al., *Virology* (1985) 140:281–288). Prehybridization, hybridization and washing of filters were done at a temperature of 33° C.

Ten separate plaques corresponding to ten different positive signals were picked, replated, and rehybridized until all were plaque purified. The inserts on these ten clones were sized by EcoRI digestion. A clone with an approximately 1.7 kb insert, designated LeEF-1, was chosen for further analysis. The EcoRI fragment of LeEF-1 was subcloned into pUC19 (Yanisch-Perron et al., *Gene* (1985) 33:103–119) yielding pCGN666. This EcoRI fragment was also cloned in both orientations into M13mp19 yielding pCGN667 and pCGN668, and into Bluescript M13+KS (Stratagene), yielding pCGN669 and pCGN670. These subclones were used for sequence analysis and generation of $^{35}$S-RNA probes. The cDNA sequence of pCGN666 has been filed with the EMBO Gene Bank Data Library Postfach 10.2209, Meyerhofstrasse 1, 6900 Heidelberg, West Germany, on Mar. 6, 1989. The file number is X14449.

Sequencing Analysis

The cDNA in pCGN670 was sequenced in the 5' to 3'direction using ExoIII-S1 nuclease nested deletions (SacI, BamHI double digested) (these deletions were made using the Promega Biotec Erase A-Base kit according to manufacturer's instructions). The dideoxy method (Sanger, et al., *Proc. Natl. Acad. Sci. USA* (1977) 74:5463–5467 was used to sequence subclones from the deletion series. To overcome gaps not covered by the nested deletions, oligomers were synthesized (Applied Biosystems 380 A synthesizer, Foster City, Calif.) based on known sequences from the previously sequenced subclones. The oligomers served as primers for the pCGN667 template. For sequence confirmation, the EF-1α cDNA was also sequenced in the 3' to 5' direction using the Sanger method on pCGN668 utilizing synthetic oligomer primers. To sequence the region nearest the polyA+ tail in pCGN668, the Maxam-Gilbert method (Maxam and Gilbert, *Proc. Natl. Acad. Sci. USA* (1977) 74:560–564) was used, sequencing through the polyA+ tail and a small distance beyond, to overlap with the previously obtained sequence.

Isolation of RNA and Northern Analysis

Tissue from various anatomical parts and developmental stages of tomato cultivar UC82B was frozen in liquid nitrogen until needed for analysis. From mature three and a half month old greenhouse grown tomato plants (UC82B), the following tissue was taken: mature leaf, mature root, young leaf, green fruit, turning fruit, and red fruit (fruit ripening stages were determined from Color Classification Requirements in Tomato, USDA Visual Aid TM-:1; February, 1975, The John Henry Co., P.0. Box 17099, Lansing, Mich.). The entire compound leaf (stem included with leaflets) was harvested to isolate mature leaf RNA. Mature root RNA was isolated from the cleaned-up root ball. Young leaves were collected as axillary shoots (about five inches from base to top). Tissue from young root was collected from one and one-half week old germinated seedlings of UC82B. Seeds were surface sterilized in a 0.1% sodium hypochlorite, 0.1% Tween 20 (Sigma Chemical Co.) solution for 15 minutes, rinsed in sterile, distilled water and germinated on moistened autoclaved germinating paper (Anchor Paper Co., St. Paul, Minn.).

Tomato total RNA was prepared as described in Colbert, et al., *Proc. Natl. Acad. Sci. USA* (1983) 80:2248-2252 with a slight modification (Facciotti, et al., *Bio/Technology* (1985) 3:241-246). PolyA+ mRNA was isolated by oligolt cellulose column chromatography as described in Colbert, et al. (1983) supra: Maniatis, et al., *Molecular Cloning: A Laboratory Manual*, Cold Spring Harbor, N.Y. (1982).

Northern analysis using nick-translated probes was performed as described (Facciotti, et al., supra). When olignoucleotides were used as probes for Northern analysis, the procedure was performed as described in O'-Neal, et al., *Nucl. Acids Res.* (1987) 15:8661-8667, except that the final washes were with 0.5×SSC, 0.1% SDS at 45° C., for 2×15 min.

DNA Isolation and Southern Analysis

Bacteriophage DNA was isolated from crude cell lysates with the Lambda Sorb (Promega Biotech) phage absorbent using the manufactuer's protocol. Tomato genomic DNA was isolated by the CTAB (cetyltrimethlammonium bromide) procedure (Taylor and Powell, *Focus* (1982) 4:4-6). Southern analysis was performed as described in Shewmaker, et al., (1985), supra.

In vitro translation analysis

Poly(A+) mRNA was isolated from the fruit of cultivar "UC 82B" by the method of Sheehy, et al., *Mol. Gene. Genet.* (1987) 208:30-36. Approximately 0.5 μg of polyA+ RNA was translated in a reticulocyte lysate (Promega Biotech) as described by the manufacturer. $^{35}$S-methionine-labelled translation products were precipitated with five volumes of acetone and collected by centrifugation. Samples were subjected to nonequilibrium two-dimensional gel electrophoresis as described by Garcia, et al., *J. Bact.* (1980) 142:196-201.

$^{35}$S-RNA Probe Generation

Sense and antisense $^{35}$S-RNA probes were generated from pCGN669 and pCGN670 respectively using T3 polymerase an an in vitro transcription reaction. These plasmids were linearized at a unique BamHI site within the Bluescript polylinker. DNA was purified after BamHI digestion by extracting with phenol twice and phenol/chloroform/isoamyl alcohol (25:24:1) once. The extracted DNA was then ethanol precipitated and was resuspended in sterile water at a concentration of 2 μg/l. In an RNase-free microfuge tube, the following were mixed in the order given: 2 μl 5× transcription buffer (200 mM Tris, pH7.5, 30 mM MgCl$_2$, 10 mM spermidine), 0.5 μl 100 mM DTT, 0.5 μl RNase inhibitor (RNasin) (25 U/μl, Promega Biotech), 2 μl 10× rNTPs (2.5 mM GTP, 2.5 mM ATP, 2.5 mM CTP, 75 μM UTP), 4.5 μl α-$^{35}$S-UTP (10 μCi/μl, New England Nuclear), 0.5 μl DNA (2 μg/μl), and 0.5 μl T3 polymerase (50 U/μl, Stratagene). After careful mixing, the reaction mixture was incubated at 37° C. for one hour. After one hour, 0.5 μl RNasin (25 U/μl, Promega Biotech) and 0.5 μl RQ1 DNAse (1 U/μl, Promega Biotech) were added and the reaction incubated for an additional 10 minutes. The reaction was stopped by the addition of 1 μl 250 mM EDTA, pH 7.0. Unincorporated ribonucleotide triphosphates were separated from RNA transcripts by Sephadex G-75 gel filtration chromotagraphy. Both pCGN669 and pCGN670 had labeled peaks of approximately $4.0 \times 10^8$ cpm/μg RNA.

In situ RNA Hybridization

Root tips from one and one-half week old tomato seedlings were fixed in a 4% paraformaldehyde/phosphate buffered saline (PBS)/5mM MgCl$_2$ solution, pH 7.4 (PBS is 10 mM pH 7.4 phosphate buffer, made to 150 mM NaCl) (Singer, et al., *Biotechniques* (1985) 4:230-250). Tissue was fixed overnight. After fixation, the tissue was passed through a graded tertiary butyl alcohol (TBA) series starting at 50% TBA, infiltrated with Paraplast and cast into paraffin blocks for sectioning, (Berlyn and Miksche (1976) *Botanical Microtechnique and Cytochemistry*, State University Press, Ames, Iowa). Embedded root tips were sectioned longitudinally on a Reichert Histostat rotary microtome at 4 μM to achieve a one-cell layer thickness. Paraffin ribbons holding 7–10 root tip sections were affixed to gelatin-chrom alum subbed slides (Berlyn and Miksche (1976), supra) and held in a dust-free box until in situ hybridizations were performed. Slides ready to be hybridized were deparaffinized in xylene and rehydrated by passing through an ethanol hydration series as described in Singer, et al., *Biotechniques* (1986) 4:230-250.

A 2× hybridization mix was made consisting of 100 μl 20× SSC, 20 μl 10% BSA, 100 μl 750 mM DDT, 200 μl 50% dextran sulfate, 50 μl RNasin, and 30 μl sterile water. 2.5 μl tRNA (20 mg/ml), 2.5 μl salmon sperm DNA (10 mg per ml) and $4 \times 10^6$ cpm probe were dried down on a lyophilizer. This mix was then resuspended in 25 μl 90° C. formamide and 25 μl 2× hybridization mix per slide. 40 μl of this hybridization mix was placed on each slide. A cover slip was placed over the sections and edges sealed with rubber cement. Slides were placed in slide holders inside a glass slide box, covered, and placed in a 37° C. dry oven overnight to hybridize. Post-hybridization treatments were as described in Singer, et al., (1986), supra.

Autoradiography was performed as described in *Kodak Materials for Light Microscope* (1986) (available from Kodak), using Kodak liquid emulsion NTB-3. Slides were exposed in a lighttight-box for approximately two weeks. After developing the autoradiographic slides, root sections were stained in 0.05% toluidine blue and then dehydrated through a graded alcohol series: xylene: 100% ethanol, 1:1, followed by 2 changes 100% xylene. Slides were left for five minutes in each solution. Coverslips were mounted with cytoseal (VWR) and left on a slide warmer until dry (45°-50° C., 1-2 days). Autoradiographic slides were then ready for microscopic examination and photomicrography.

B. Results

To isolate a tomato EF-1α cDNA clone, a fragment from a *Mucor racemosa* EF-1α cDNA clone was used (Linz and Sypherd, *Mol. Cell Biol.* (1987) 7:1925-1932). Preliminary analysis using this probe to tomato RNA indicated that under the conditions used, the Mucor probe hybridized solely to a bind of approximately 1.8 kb. This agrees with the size reported for other EF-1α cDNA RNA's (Nagata, et al., *EMBO J.* (1984) 3:1825-1830; Linz et al., *Mol. Cell Biol.* (1986) 6:593-600), and is within the expected size range of the protein (45-55 kd).

The clone containing the largest insert of 1.7 kb, hereinafter termed LeEF-1, was chosen for further analysis.

LeEF-1 contains 60 nucleotides upstream of the ATG, a 1344 nucleotide (448 amino acids) coding region and 284 nucleotides of 3'-untranslated region. In the 5'-untranslated region there are two in-frame stop codons. In-frame stop codons are also found in the 5' untranslated regions of other EF-1α genes. In the LeEF-1, an adenine residue is at the −3 position and a guanine residue is at the +4 position relative to the start AUG codon. This nucleic acid sequence surrounding the initiator codon displays the consensus signal for efficient translation initiation. The complete sequence of LeEF-1 is shown in FIG. 1.

Amino acid sequence comparisons between the polypeptides encoded by tomato EF-1α gene, LeEF-1 and an EF-1α gene from Mucor, as well as Artemia, yeast, and man show substantial homology. The LeEF-1 gene product is 76% homologous to that of yeast and Mucor; 75% homologous to that of Artemia; and 78% homologous to that of man.

As shown in FIG. 2, one notable difference between LeEF-1 and the four other eukaryotic EF-1α's is that a 12 amino acid gap must be introduced between amino acids 213 and 214 of the protein encoded by LeEF-1 to provide maximum homology to the other eukaryotic EF-1α gene products. The homology between the polypeptides encoded by the four other eukaryotic EF-1α genes in this gap region ranges from 29% to 64% and no specific function has been previously assigned to this region.

EF-1α Is A Multigene Family In Tomato

To determine if EF-1α in tomato was encoded by one or multiple genes, Southern blot analysis was performed. When tomato DNA restricted with EcoRI was hybridized to LeEF-1, at least six distinct bands were seen. This indicated that EF-1α is probably a multigene family. This was verified by screening a tomato genomic library for EF-1α clones. Six distinct clones obtained from this screen were restricted with EcoRI and hybridized to LeEF-1. These six distinct clones represent four of the bands seen on the genomic Southern blot. The EcoRI fragment from one of these clones (61-1) was subcloned and shown to contain an entire EF-1α gene (see Example II). While it is clear that EF-1α in tomato is a multigene family, the exact size of the family remains to be determined.

EF-1α Is Expressed In Rapidly Growing Tissue

Various tomato mRNA's were run on a Northern gel and hybridized against the tomato EF-1α cDNA. Specifically, the probe was the 1.7 kb EcoRI fragment from pCGN666 which had been labelled by nick-translation. Tissues chosen for analysis were young leaf, young root, mature leaf, mature root, green tomato fruit, turning tomato fruit, and red ripe tomato fruit. Significant levels of EF-1α mRNA were found in all tissues examined with values ranging from 0.1 to 1.0% of total mRNA. Levels of EF-1α mRNA decreased in both the leaves and roots as they matured and in the fruit as it ripened.

The expression pattern of EF-1α was further examined in vitro translation. Poly(A+) RNA from green and red (mature) tomato fruit was isolated, translated and subjected to 2-D gel analysis. The EF-1α protein is easily identifiable because of its molecular weight (50,000 daltons) and its high pI of around 9. While EF-1α protein is produced from mRNA of both green and red fruit, more is produced by the RNA from younger green fruit. These data, taken together with the Northern analysis, indicate that EF-1α is a highly expressed protein in tomato and that this expression is greater in young, rapidly growing tissue than in older, more mature tissue.

5. Localization of EF-1α, RNA To Meristematic Regions of The Root Tip

To further characterize the expression pattern of EF-1α, in situ hybridizations were performed. In root tips there are well-defined meristematic regions that are associated with active cell division as well as regions associated with cell elongation (Raven, et al., *Biology of Plants* (1976); Essau, *Anatomy of Seed Plants* (1977); Galston, et al., *The Life of The Green Plant* (1980)). When 4-mm root tips from young tomato plants were hybridized to sense and antisense $^{35}$S-EF-1α RNA, the antisense transcripts hybridized to distinct regions of the root tips, while the sense transcripts (negative control) showed no hybridization. More hybridization was seen in the first 1 to 2 mm of the root tip, which corresponds to the region of cell division, than in the tissue further up the root tip, known as the region of cell elongation. Strong, defined hybridization was seen in the three primary meristems: protoderm, ground meristem, and procambrium, as well as in the apical meristem. The three meristems in a root give rise to the epidermis, cortex and primary vascular tissue respectively. Thus, within a root tip, the highest levels of EF-1α mRNA were found in meristematic or rapidly dividing cells. In summation, these in situ results corroborated the Northern data to demonstrate that EF-1α mRNA in tomato is particularly abundant in actively dividing cells.

Example II

ISOLATION AND CHARACTERIZATION OF AN EF-1α GENOMIC CLONE 61-1

A. Materials and Methods

1. Screening a tomato genomic library for EF-1α genomic clones.

A tomato (*Lycopersicon esculentum* cv 'T6') partial EcoRI genomic library was provided by Dr. Robert Goldberg, UCLA. This library was screened for EF-1α genes using the nick-translated tomato cDNA, LeEF-1 as a probe. Approximately eight tomato genome equivalents in 800,000 plaques of the Charon4 phage in *E. coli* host LE392 (F⁻hsdR514 supE44 supF58 lacY1 or lac(1-Y6 galK2 galT22 metB1 trpR55 9λ⁻) were screened. DNA was transferred to Gene Screen Plus filters as described in Example I for screening the tomato cDNA. Prehybridization, hybridization, and washing of filters were as described in Shewmaker, et al. (1985), supra). Filters were prehybridized and hybridized at 42° C. and washed at 55° C. A number of positive plaques were picked and replated until plaque purified. The tomato inserts in positive clones were sized by EcoRI digestion.

2. Isolation, mapping and sequencing of an EF-1α genomic clone (61-1) from tomato.

a. Construction of pCGN2123

One EF-1α lambda clone (61-1) containing a 5.6 kb EcoRI fragment that hybridized to LeEF-1 was chosen for further analysis. DNA from 61-1 was prepared using a Lambda Sorb kit (Promega Biotech) according to manufacturer's instructions. The 5.6 kb EcoRI piece was subcloned into pUC19 yielding pCGN2123. Using standard mapping techniques (Maniatis, et al., (1982) *Molecular Cloning, A Laboratory Manual,* Cold Spring Harbor, N.Y.), the approximately 2 kb EF-1α gene was located within the 5.6 kb fragment. The coding region plus approximately 800 bp 5' of the start codon and approximately 1200 bp 3' of the stop codon were sequenced. Sequence analysis was performed using standard techniques, similar to those described for the sequencing of LeEF-1.

3. Construction of Binary Plasmid pCGN783 pCGN783 is a binary plasmid containing the left and right T-DNA borders of *A. tumefaciens* (Currier and Nester, *J. Bacteriol,* (1976), 126:157-165); the gentamicin resistance gene of pPH1JI (Hirsch, et al., *Plasmid* (1984) 12:139-141); the 35S promoter of cauliflower mosaic virus (CaMV) (Gardner, et al., *Nucleic Acids Res.* (1981) 9:2871-2888); the kanamycin resistance gene of Tn5 (Jorgenson et al., *Mol. Gen. Genet.,* (1979) 177:65-); and the 3' region from transcript 7 of pTiA6 (Currier and Nester (1976), supra). pCGN783 was constructed by the multistep process described below. pCGN783 has been deposited with the American Type Culture Collection (ATCC 67868).

Construction of pCGN451 pCGN451 contains the ocs5'-ocs3' cassette cloned into a derivative of pUC8 (Vieira and Messing, *Gene,* (1982), 19:259-268). The modified vector was derived by digesting pUC8 with HincII and ligating in the presence synthetic linker DNA, creating pCGN416, and then deleting the EcoRI site of pCGN416 by EcoRI digestion followed by treatment with Klenow enzyme and self ligation to create pCGN426.

The ocs5'-ocs3' cassette was created by a series of steps from DNA derived from the octapine Ti-plasmid pTiA6 (Currier and Nester, *J. Bact.* (1976) 126:157-165). An EcoRI fragment of pTiA6 (bp 13362-16202; the numbering is by Barker, et al., *Plant mol. Biol.* (1983) 2:335-350), for the closely related Ti plasmid pTi15955) was removed from pVK232 (Knauf and Nester, *Plasmid* (1982) 8:45) by EcoRI digestion and cloned into EcoRI digested pACYC184 (Chang and Cohen, *J.Bacteriol.* (1978) 134:1141-1156) to generate pCGN15.

The 2.4 kb BamHI-EcoRI fragment (bp 13774-16202) of pCGN15 was cloned into EcoRI-BamHI digested pBR322 (Bolivar, et al., *Gene* (1977) 2:95-113) to yield pCGN429. The 412 bp EcoRI-BamHI fragment (bp13362-13774) of pCGN15 was cloned into EcoRI-BamHI digested pBR3322 (Bolivar, et al., *Gene* (1977) 2:95-113) to yield pCGN407. The cut-down promoter fragment was obtained by digesting pCGN407 with XmnI (bp 13512), followed by resection with Bal31 exonuclease, ligation of synthetic EcoRI linkers, and digestion with BamHI. Resulting fragments of approximately 130 bp were gel purified and cloned into M13mp9 (Vieira and Messing, *Gene* (1982) 19:259-268 and sequenced. A clone, I-4, in which the EcoRI linker had been inserted at bp 13642 between the transcription initiation point and the translation initiation codon was identified by comparison with the sequence of de Greve et al (de Greve, et al., *J. Mol. Appl. Genet.* (1982) 1:499-512). The EcoRI cleavage site was at position 13639, downstream from the mRNA start site. The 141 by EcoRI-BamHI fragment of I-4, containing the cut-down promoter, was cloned into EcoRI-BamHI digested pBR322 (Bolivar, et al., *Gene* (1977) 2:95-113) to create pCGN428. The 141 bp EcoRI-BamHI promoter piece from pCGN428, and the 2.5 kb EcoRI-BamHI ocs 5' piece from pCGN429 were cloned together into EcoRI digested pUC9 (Vieira and Messing, *Gene* (1982) 19:259-268) to generate pCGN442, reconstructing the ocs upstream region with a cut-down promoter section.

The HindIII fragment of pLB41 (D. Figurski) containing the gentamicin resistance gene was cloned into HindIII digested pACYC184 (Chang and Cohen, *J. Bacteriol.* (1978) 134:1141-1156) to create pCGN413b. The 4.7 kb BamHI fragment of pTiA6 (Currier and Nester, *J. Bact.* (1976) 126:157-165) containing the ocs 3' region, was cloned into BamHI digested pBR325 (F. bolivar, *Gene* (1978) 4:121-136) to create 33c-19. The SmaI site a position 11207 of 33c-19 was converted to an XhoI site using a synthetic XhoI linker, generating pCGN401 2. The 3.8 kb BamHI-EcoRI fragment of pCGN401.2 was cloned into BamHI-EcoRI digested pCGN413b to create pCGN419.

The ocs5'-ocs3' cassette was generated by cloning the 2.64 kb EcoRI fragment of pCGN442, containing the 5' region, into EcoRI digested pCGN419 to create pCGN446. The 3.1 kb XhoI fragment of pCGN446, having the ocs 5' region (bp 13639-15208) and ocs 3' region (bp 11207-12823), was cloned into the XhoI site of pCGN426 to create pCGN451.

Construction of pCGN587 pCGN587 was prepared as follows: The HindIII-SmaI fragment of Tn5 containing the entire structural gene for APH3'II (Jorgensen, et al., *Mol. Gen. Genet.* (1979) 177:65) was cloned into HindIII-SmaI digested pUC8 (Vieira and Messing, *Gene* (1982) 12:259-268). This converted the fragment into a HindIII-EcoRI fragment, since there was an EcoRI site immediately adjacent to the SmaI site. The PstI-EcoRI fragment of pCGN300, containing the 3'-portion of the APH3'II gene, was then combined with an EcoRI-BamHI-SalI-PstI linker into the EcoRI site of pUC7 to make pCGN546W. An ATG codon was upstream from and out of reading frame with the ATG initiation codon of APH3'II. The undesired ATG was avoided by inserting a Sau3A-PstI fragment from the 5'-end of APH3'II, which fragment lacks the superfluous ATG, into the BamHI-PstI site of pCGN546W to provide plasmid pCGN550. The EcoRI fragment of pCGN550 containing the APH3'II gene was then cloned into the EcoRI site of pUC8-pUC13-cm (K. Buckley, Ph.D. Thesis, UC San Diego, (1985)) to give pCGN551. The plasmid pCGN451 having the ocs 5' and ocs 3' in the proper orientation was digested with EcoRI and the EcoRI fragment from pCGN551 containing the intact kanamycin resistance gene inserted into the EcoRI site to provide pCGN552 having the kanamycin resistance gene in the proper orientation. This ocs/KAN gene was used to provide a selectable marker for the trans type binary vector pCGN587.

The 5' portion of the engineered octopine synthase promoter cassette consisted of pTiA6 DNA from the XhoI site at bp 15208-13644 (Barker, et al., Plant Mol. Biol. (1983) 2:335-350), and also contains the T-DNA boundary sequence (border) implicated in T-DNA transfer. In the plasmid pCGN587, the ocs/KAN gene from pCGN552 provided a selectable marker as well as the right border. The left boundary region was first cloned in M13mp9 as a HindIII-SmaI piece (pCGN502) base pairs 602-2212 and recloned as a KpnI-EcoRI fragment in pCGN565 (a cloning vector containing vector based upon pUC8-cm but containing pUC18 linkers) to provide pCGN580. pCGN565 is a cloning vector based on a pUC8-pUC13-cm (K. Buckley, (1985), supra) but containing pUC18 linkers (Yanisch-Perron, et al., Gene (1985) 33:103-119) pCGN580 was linearized with BamHI and used to replace the smaller BglII fragment of pVCK102 (Knauf and Nester, Plasmid (1982) 8:45), creating pCGN585. By replacing the smaller SalI fragment of pCGN585 with the XhoI fragment from pCGN552 containing the ocs/KAN gene, pCGN587 was obtained.

Construction of pCGN739 (Binary Vector)

To obtain the gentamicin resistance marker, the gentamicin-resistance gene was isolated from a 3.1 kb EcoRI-PstI fragment of pPHIJ1 (Hirsch, et al., (1984), supra) and cloned into pUC9 (Vieira and Messing, Gene (1982) 19:259-268) yielding pCGN549. The HindIII-BamHI fragment from pCGN549 containing the gentamicin-resistance gene replaced the HindIII-BglII fragment of pCGN587, creating pCGN594. The pCGN594 HindIII-BamHI region, which contains a 5'-ocs-kanamycin-ocs-3' (ocs is octopine synthase with 5' designating the promoter region and 3' the terminator region, see co-pending U.S. application Ser. No. 834,161, filed Feb. 26, 1986) fragment was replaced with the HindIII-BamHI polylinker region from pUC18 (Yanish-Peron, et al, Gene (1985) 33:103-119) to make pCGN739.

Construction of pCGN734

The HindIII-SphI fragment of pTiA6 corresponding to bases 3390-3241 (Barker, et al., Plant Mol. Biol. (1983) 2:335-350) was cloned into the HindIII-SphI site of M13mp19 (Yanisch-Perron, et al., Gene (1985) 53:103-119; Norrander, et al., Gene (1983) 26:101-106). Using an oligonucleotide corresponding to bases 3287 to 3300, DNA synthesis was primed from this template. Following S1 nuclease treatment and HindIII digestion, the resulting fragment was cloned in the HindIII-SmaI site of pUC19 (Yanisch-Perron, et al., Gene (1985) 33:103-119). An EcoRI-HindIII fragment corresponding to bases 3287-3390 (Barker, et al., Plant mol. Biol. (1983) 2:335-350) was cloned with the EcoRI-HindIII fragment of pTiA6 (corresponding to bases 3390-4494) into the EcoRI site of pUC8 Vieira and Messing, Gene (1982) 19:259-268) resulting in pCGN734.

Construction of pCGN726c pCGN556 contains the EcoRI-HindIII linker of pUC18 (Yanisch-Perron, et al., Gene (1985) 33:103-119) inserted into the EcoRI-HindIII sites of pUC13-cm (K. Buckley (1985), supra). The HindIII-BglII fragment of pNW31c-8,29-1 (Thomashow, et al., Cell (1980) 19:729-739) containing ORF1 and 2 of pTiA6 (Barker, et al., Plant Mol. Biol. (1983) 2:335-350) was subcloned into the HindIII-BamHI sites of pCGN556 producing pCGN703.

The Sau3A fragment of pCGN703 containing the 3' region of transcript 7 (corresponding to bases 2396-2920 of pTiA6 (Barker, et al., (1983) supra) was subcloned into the BamHI site of pUC18 producing pCGN709. The EcoRI-SmaI polylinker region of pCGN709 was replaced with the EcoRI-SmaI fragment of pCGN587, which contains the kanamycin resistance gene (APH3-II) producing pCGN726.

The EcoRI-SalI fragment of pCGN726 plus the BglII-EcoRI fragment of pCGN734 were inserted into the BamHI-SalI site of pUC8-pUC13-cm (chloramphenicol resistant, K. Buckely, (1985), supra) producing pCGN738. pCGN726c was derived from pCGN738 by deleting the 900 bp EcoRI-EcoRI fragment.

Construction of pCGN528 (Shuttle Vector)

pCGN525 was made by digesting a plasmid containing Tn5 which harbors a kanamycin gene (Jorgenson, et al., Mol. Gen. Genet. (1979) 177:65) with HindIII-BamHI and inserting the HindIII-BamHI fragment containing the kanamycin gene into the HindIII-BamHI sites into the tetracycline gene of pACYC184 (Chang and Cohen, J. Bacteriol. (1978) 134:1141-1156). pCGN526 was made by inserting the BamHI fragment 19 of pTiA6 (Thomashow, et al., Cell (1980) 19:729-739), modified with XhoI linkers inserted into the SmaI site, into the BamHI site of pCGN525. pCGN528 was obtained by deleting the small XhoI fragment from pCGN526 by digesting with XhoI and religating.

Construction of pCGN167

The AluI fragment of CaMV (bp 7144-7735) (Gardner, et al., Nucl. Acid Res. (1981) 9:2871-2888) was obtained by digestion with AluI. It was then cloned into the HincII site of M13mp7 (Messing, et al., Nucl. Acids Res. (1981) 9:309-321) to create C614. An EcoRI digest of C614 produced the EcoRI fragment from C614 containing the 35S promoter which was cloned into the EcoRI site of pUC8 (Vieira and Messing, Gene (1982) 19:259-268) to produce pCGN146. To trim the promoter region, the BglII site (bp 7670) was treated with BglII and resected with Bal31. Subsequently a BglII linker was attached to the Bal31 treated DNA to produce pCGN147.

pCGN148a, containing a promoter region, selectable marker (KAN with 2 ATG's) and 3' region, was prepared by digesting pCGN528 with BglII and inserting the BamHI-BglII promoter fragment from pCGN147. This fragment was cloned into the BglII site of pCGN528 so that the BglII site was proximal to the kanamycin gene of pCGN528.

pCGN149a was made by cloning the BamHI-kanamycin gene fragment from pMB9KanXXI into the BamHI site of pCGN148a. pMB9KanXXI is a pUC4 variant (Vieira and Messing, Gene (1982) 19:259-268) which has the XhoI site missing but contains a functional kanamycin gene from Tn903 to allow for efficient selection in Agrobacterium. pCGN149a was digested with BglII and SphI. This small BglII-SphI fragment of pCGN149a was replaced with the BamHI-SphI fragment from MI (see below) isolated by digestion with BamHI and SphI. This produces pCGN167, a construct containing a full length CaMV promoter, 1ATG-kanamycin gene, 3' end and the bacterial TN903-type kanamycin gene. MI is an EcoRI fragment from pCGN550 (see construction of pCGN587) and was cloned into the EcoRI cloning site of M13mp9 so that the PstI site in the 1ATG-kanamycin gene was proximal to the polylinker region of M13mp9.

Construction of pCGN766c (35S promoter-3' region)

The HindIII-BamHI fragment of pCGN167 containing the CaMV-35S promoter, 1ATG-kanamycin gene and the BamHI-fragment 19 of pTiA6 was cloned into the BamHI-HindIII sites of pUC19 (Yanisch-Perron (1985), supra) creating pCGN976. The 35S promoter and 3' region from transcript 7 was developed by inserting a 0.7 kb HindIII-EcoRI fragment of pCGN976 (35S promoter) and the 0.5 kb EcoRI-SauI fragment of pCGN709 (transcript 7:3') into the HindIII-SalI sites of pCGN566 (pCGN566 contains the EcoRI-HindIII linker of pUC18 inserted into the EcoRI-HindIII sites of pUC13-Cm) creating pCGN766c.

Final Construction of pCGN783

The 0.7 kb HindIII-EcoRI fragment of pCGN766c (CaMV-35S promoter) was ligated to the 1.5 kb EcoRI-SalI fragment of pCGN726c (1ATG-Kan 3' region) followed by insertion into the HindIII-SalI fragment of pCGN778 containing the CaMV-35S promoter and 1ATG-KAN-3' region was used to replace the HindIII-SalI linker region of pCGN739 to produce pCGN783.

4. Construction of pCGN2125, an EF-1α GUS Fusion Construct

To analyze the expression of 61-1 when reintroduced into tomato plants, the GUS (β-glucuronidase, *E. coli*) gene was inserted into the coding region of 61-1. The fusion was done so that the GUS coding region was inframe with the EF-1α sequence so that a protein with GUS activity could be produced.

a. Construction of pCGN2125

To construct pCGN1804, the approximately 2 kb BamHI-SstI fragment from pBI221 containing the GUS gene (Jefferson, *Plant Mol. Biol. Reporter* (1987) 5:387–405) was cloned into pUC119. To construct pCGN2124, pCGN2123 (see Example II A.2.a.) was linearized with ClaI, and treated with the Klenow fragment of DNA polymerase I to blunt the ends. The resulting DNA was ligated to the BamHI-EcoRI fragment of pCGN1804, containing the GUS gene, which had also been treated with the Klenow fragment of DNA polymerase. A clone, pCGN2124, was chosen that had this fragment inserted in the correct orientation. The ClaI/BamHI junction between EF-1α and GUS was sequenced to verify that the GUS insertion was in-frame with the EF-1α coding region. The fusion contained the first 34 amino acids of EF-1α from 61-1 and 8 amino acids of linker region followed by the GUS gene.

To facilitate transfer to tomato plants, pCGN2124 was inserted into the *Agrobacterium tumefaciens* binary vector, pCGN783 (see above). pCGN2124 was linearized with SalI and inserted into the SalI site of pCGN783 (supra). A clone, pCGN2125, with the EF-1α GUS gene being transcribed in the same direction as the 35S-kan-tml gene was obtained. This construct in the *Agrobacterium tumefaciens* LBA4404 (also referred to as 2760) was used to transform tomato plants.

5. Construction of pCGN7001 (mas-gus-mas construct)

To evaluate levels of GUS produced from pCGN2125 in tomato plants, tomato plants containing a mas-gus-mas construct (pCGN7001) were generated. The mas (mannopine synthase promoter) has been previously studied and shown to give a relatively low level of expression (Murai and Kemp, *Nucl. Acids Res.* (1982) 10:1679–1689).

To construct pCGN7001, a 5' mas-gus-mas 3' sequence was inserted into the SalI site of pCGN783. The 5' mas-gus-mas 3' construct contained sequentially the following sequences: Xho linker; the NaeI to blunted ClaI fragment of the T-DNA of pTiA6 which spans the nucleotides 20806 to 20128 (the numbering is by Barker, et al., *Plant Mol. Biol.* (1983) 2:335–350 for the closely related Ti plasmid pTi 15955); the AccI to BamHI linker region of pUC19; the BamHI to SstI fragment of pCGN1804 containing the β-glucuronidase gene; the SstI to EcoRI linker region of pUC19; EcoRI linker; the blunted HindIII to blunted SstI fragment of pTiA6 which spans the nucleotides 19239 to 18462; (Barker, et al., supra); Xho linker.

The 5' mas-gus-mas 3' sequence was inserted into pCGN783 so that the 5' mas-gus-mas 3' sequence was transcribed in the same direction as the 35S-kan-tml gene. This construct in the *Agrobacterium tumefaciens* LBA4404 was used to transform tomato plants.

6. Transformation of Tomato Cotyledon Tissue a. Preparation of *A. tumefaciens* LBA 4404/pCGN7001 and pCGN2125

The plasmids pCGN7001 or pCGN2125, respectively, were transformed into *E. coli* C2110 (polA) as follows.

Bacterial matings were performed using two *E. coli* strains and *Agrobacterium tumefaciens* strain LBA4404. One *E. coli* strain (MM294) harbored pRK2073 which provided mobilization functions and the other strain (C2110) carried the plasmid with a kanamycin resistance marker to be transferred into Agrobacterium. The two *E. coli* strains were grown overnight at 37° C. with shaking in LB broth. The Agrobacterium strain was grown overnight at 28° C. in MG/L broth. Fifty microliters of each of the three strains were mixed on a nitrocellulose filter placed on an MG/L plate. The plate was incubated at 28° C. for 3 days. The mixture was then streaked onto an AB minimal medium supplemented with 100 μg/ml kanamycin and 100 μg/ml streptomycin and incubated at 28° C. for two days. The streptomycin was included to kill the two *E. coli* strains. Single colonies were picked and purified by two more streakings on the above medium.

b. Transformation of Tomato Cotyledon Tissue with pCGN7001 and pCGN2125

Substantially sterile tomato cotyledon tissue was obtained from seedlings which had been grown at 24° C., with a 16 hr/8 hr day/night cycle in 100×25 mm Petri dishes containing Murashige-Skoog salt medium and 0.8% agar (pH 6.0). Any tomato species may be used, however, here the inbred breeding line was UC82B, available from the Department of Vegetable Crops, University of California, Davis, Calif. 95616. The cotyledons were cut into three sections and the middle section placed onto feeder plates for a 24-hour preincubation. The feeder plates were prepared by pipetting 0.5 ml of a tobacco suspension culture ($\sim 10^6$ cells/ml) onto 0.8% agar medium, containing Murashige minimal organic medium (K. C. Biologials), 2,4-D (0.2 mg/L), kinetin (0.1 mg/L), thiamine (0.9 mg/L) and potassium acid phosphate (200 mg/L, pH 5.5). The feeder plates were prepared two days prior to use. A sterile 3 mm filter paper disk containing feeder medium was placed on top of the tobacco cells after the suspension cells had grown for two days.

Following the preincubation period, the middle segments of the cotyledon sections were placed into a liquid MG/L broth culture (1-5 ml) of the *Agrobacterium tumefaciens* strain LBA4404/pCGN7001 or pCGN2125 ($1 \times 10^7$-$1 \times 10^8$ bacteria/ml). The cotyledon sections were cocultivated with the bacteria for 48 hrs. on the feeder plates and then transferred to regeneration medium containing 350 mg/L cefotaxime and 100 mg/L kanamycin. The regeneration medium is a K. C. Biologicals Murashige-Skoog salts medium with zeatin (2 mg/L), myo-insitol (100 mg/L), sucrose (20 g/L), Nitsch vitamins and containing 0.8% agar (pH 6.0). In 2 to 3 weeks, shoots developed. When the shoots were approximately 1.25 cm, they were excised and transferred to a Murashige and Skoog medium containing cefotaxime (350 mg/L) and kanamycin (50 mg/L for rooting. Roots developed within 10-12 days.

7. Analysis of GUS Expression in Transformed Tomato Seedlings

Young leaf tissue was excised from tomato plantlets that were growing from the cut edges of cotyledons that had been co-cultivated with *Agrobacterium tumefaciens* containing pCGN2125 or pCGN7001 constructs 6-8 weeks previously. The tissue was grown on medium containing 100 mg/ml kanamycin; 350 mg/ml cefotaxime (Cal Biochem-Hoechst). The remainder of the medium was 22 medium (Murashige and Skoog salts 2% sucrose, 100 mg/l myoinositol, Nitsch vitamins, 2 mg/l zeatin and 0.8% Bactoagar). One plantlet from cocultivation with pCGN7001 were chosen for further analysis.

The fluorimetric GUS assay was performed essentially as described (Jefferson et al., *EMBO J.* (1987) 6:3901-3907). Specifically, young tomato leaf tissue (0.03-0.20 g) was ground in 500 μl GUS extraction buffer (50 mM sodium phosphate, pH 7.0, 10 mM BME, 10 mM EDTA, 0.1% Triton X-100). The extract was centrifuged in a microfuge for 10 min. and the supernatant removed. Various dilutions of the supernatant in extraction buffer were made. Typically 1:10 dilutions in 500 μl total volume were analyzed. Five μl of MUG (methylumbelliferone), 100 mM in dimethylformamide, were added and the reaction mixtures incubated at 37° C. for 2 hours. The reaction was terminated by the addition of 900 μl of 0.2M Na₂CO₃. Fluorescence was measured with excitation at 365 nm, emission at 455 nm on a Farrand system 3 fluorimeter with slit widths set at 10 nm.

B. Results

1. Characterization of a EF-1α Genomic Clone

The EF-1α gene contains one intron of 320 bp. This gene encodes a polypeptide which is 97% homologous to the polypeptide encoded by LeEF-1. 61-1 is therefore one of the members of the EF-1α multigene family, but it is not the gene that gave rise to the LeEF-1 cDNA clone. The sequence of the EF-1α genomic clone, 61-1, is shown in FIG. 3.

To determine what percentage of the total EF-1 mRNA arises from the 61-1 gene and what percentage arises from the gene that gave rise to LeEF-1 (pCGN666), specific oligomers were synthesized.

Oligomer EF p27 (5'-AGCTTGTAGATCAAGT-CACCAGTGGTAGTC-3') corresponds to bases 123 to 153 of LeEF-1 and since it is in a conserved region of the coding sequence will bind to all EF-1α mRNAs. Oligomer EF p28 (5'-ACTGATATCTCTG-GTAACTCCAGAGTTGAA-3') corresponds to bases 2542 to 2572 of 61-1 in the 3'-untranslated region. This sequence is unique to 61-1. Oligomer EF p29 (5'-ATAGCATTCGAAACACCAGCATCACACTGC-3') corresponds to bases 1413 to 1443 of LEF-1 in the 3'-untranslated region. This sequence is unique to LeEF-1.

Using these three oligomer probes, Northern analysis was run on poly(A+) RNA from young axial shoots of tomato. The results demonstrated that the gene that gave rise to LeEF-1 (pCGN666) contributes a major portion of the EF-1α message. Comparing signals obtained with oligomers EFp27 and EFp29, it is possible to estimate that the gene that gave rise to LeEF-1 contributes at least 30% and perhaps as much as 50-60% of the total EF-1α mRNA. On the other hand, a comparison of the signals obtained from EFp27 and EFp28, indicates that 61-1 contributes on the order of only 1% of the total EF-1α mRNA.

2. Analysis of Tomato Plants Transformed with pCGN2125

The results of a typical assay are shown in Table 1 below.

TABLE 1

| FLUOROMETRIC GUS ASSAY | | | |
|---|---|---|---|
| Plant Sample | Weight of Sample | Fluorescence Intensity (F) of 1/10 Dilution | Fluorescence Intensity (F) normalized to 0.1 g Sample |
| 2125-X | 0.04 g | 163 | 408 |
| 7001-A | 0.14 g | 311 | 222 |

The GUS levels produced by the 2125 (EF-1α GUS) plant are similar to those produced by a 7001 (mas-gus) plant. The level of EF-1α mRNA produced by the native 61-1 gene is approximately 1% of the total EF-1α RNA. Since the total EF-1α mRNA level is approximately 1% of the poly(A+) RNA, then the mRNA produced by the 61-1 gene represents about 0.01% of the poly(A+) RNA. The message produced from the mannopine synthase promoter is low level and may be equal to or less than that produced from the octopine synthase (ocs) promoter (Murai and Kemp, *Nucl. Acids Res.* (1982) 10:1679-1689). The level of mRNA produced from the ocs promoter averages around 0.005% and ranges from 0.002% to 0.01% of total mRNA (Comai, et al., *Nature* (1985) 317:741-744). Thus the mannopine promoter and the 61-1 EF-1α gene produce similar levels of mRNA. Thus the similar levels of GUS activity produced from the 2125 and 7001 plants are as would be predicted and indicate that the EF-1α-GUS fusion in 2125 is functioning as expected.

Example III

EF-1α Genomic Clone A, The Genomic Equivalent of pCGN666

A. Materials and Methods

1. Construction of pCGN2127

The approximately 250 bp XbaI (1464) to EcoRI fragment of pCGN666 was cloned into XbaI-EcoRI digested pUC19. This resulted in pCGN2127.

2. Probe Description, Isolation and Labelling

Probe A: The 1.7 kb EcoRI fragment of pCGN666 containing LeEF-1 was isolated and nick-translated as previously described (Shewmaker, et al., supra).

Probe B: The approximately 250 bp XbaI-EcoRI fragment of pCGN2127 was isolated and nick-translated as previously described (Shewmaker, et al., supra). This fragment contains only sequences in the 3'untranslated portion of LeEF-1.

Probe C: The 30 base oligonucleotide EFp29 (see supra) which hybridizes to nucleotides 1413 to 1443 of LeEF-1. This oligonucleotide hybridizes to sequences in the 3' untranslated region of LeEF-1 that are different from those to which probe B hybridizes.

3. Screening a Tomato Genomic Library for the Genomic Equivalent to pCGN666

A tomato (*Lycopersicon esculentum* cv VFNT-Cherry) partial Sau3A library in Ch35 (Loenen, *Gene* (1983) 26:171-179) was provided by Dr. Robert Fischer of University of California, Berkeley. The basic screening procedures were as described above in Example II. When the nick-translated probes A and B were used, hybridization and washing were as described for genomic screening. When the oligonucleotide probe C was used, hybridization and washing were as described for Northern analysis using oligonucleotide probes.

Approximately 800,000 plaques of the above library were screened with probe A. Subsequent rounds of plaque purification of positive signals were done with duplicate filters, one hybridized with probe A and the other with probe B. Only plaques that hybridized to both probes were chosen for final plaque purification. Purified plaques that hybridized to both probes A and B were also screened with probe C. A clone denoted "A" that hybridized to all 3 probes was chosen for further analysis. The EF-1α gene within A was designated LeEF-A.

4. Mapping, Subcloning and Sequencing

DNA from phage "A" was isolated as described (Grossgerger, *Nuc. Acids. Res.* (1987) 15:6737). The 11 kb insert of tomato genomic DNA within "A" and the location of LeEF-A within this insert were mapped using standard techniques. (Maniatis, Fritsch and Sambrock, *Molecular Cloning, A Laboratory Manual* (1982) Cold Spring Harbor, N.Y.) Several subclones of the insert in "A" were generated using standard cloning techniques. These subclones were used for DNA sequencing and included.

pCGN674 and pCGN675: The approximately 9 kb KpnI fragment cloned in both orientations in pUC19. This fragment contains 5' upstream regions as well as coding region from the amino terminal portion of the gene.

pCGN2134: The approximately 2.5 b EcoRI fragment cloned into pUC19. This fragment contains the coding region and region 3' of the LeEF-A gene.

Using pCGN674, pCGN674, pCGN2134 and standard sequencing techniques similar to those described supra, the sequence of (1) the coding region, (2) approximately 2.5 kb upstream of the initiation codon, and (3) approximately 0.7 kb 3' of the stop codon were obtained.

5. Construction of pCGN1558 pCGN1558 is a binary plant transformation vector containing the left and right T-DNA borders of *Agrobacterium tumefaciens* octopine Ti-plasmid pTiA6 (Currier and Nester *J. Bact.* (1976) 126:157-165), the gentamycin resistance gene of pPH1JI (Hirsch and Beringer, *Plasmid* (1984) 12:139-141), an *Agrobacterium rhizogenes* Ri plasmid origin of replication from pLJbB11 (Jouanin et al., *Mol. Gen. Genet.* (1985) 201:370-374), a 35S promoter-Kan$^R$-tml$^3$ region capable of conferring kanamycin resistance to transformed plants, a ColE1 origin of replication from pBR322 (Bolivar et al., *Gene* (1977) 2:95-113), and a lacZ' screenable marker gene from pUC18 (Yanish-Perron, et al., *Gene* (1985) 33:103-119).

Construction of pCGN1546

The 35S promoter-tml3' expression cassette, pCGN986 (contains a cauliflower mosaic virus 35S (CaMV35) promoter and a T-DNA tml 3'-region with multiple restriction sites between them. pCGN986 was derived from another cassette, pCGN206, containing a CaMV35S promoter and a different 3' region, the CaMV region VI 3'-end. The CaMV 35S promoter was cloned as an AluI fragment (bp 7144-7734) (Gardner et. al, *Nucl. Acids Res* (1981) 9:2871-2888) into the HincII site of M13mp7 (Messing, et. al, *Nucl. Acids Res.* (1981) 9:309-321) to create C614. An EcoRI digest of C614 produced the EcoRI fragment from C614 containing the 35S promoter which was cloned into the EcoRI site of pUC8 (Viera and Messing, *Gene* (1982) 19:259) to produce pCGN147.

pCGN148a containing a promoter region, selectable marker (KAN with 2 ATG's) and 3' region, was prepared by digesting pCGN528 with BglII and inserting the BamHI-BglII promoter fragment from pCGN147. This fragment was cloned into the BglII site of pCGN528 so that the BglII site was proximal to the kanamycin gene of pCGN528.

The shuttle vector used for this construct pCGN528, was made as follows: pCGN525 was made by digesting a plasmid containing Tn5 which harbors a kanamycin gene (Jorgenson et. al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134:1141-1156). pCGN526 was made by inserting the BamHI fragment 19 of pTiA6 (Thomashow et. al., *Cell* (1980) 19:729-739), modified with XhoI linkers inserted into the SmaI site, into the BamHI site of pCGN525. pCGN528 was obtained by deleting the small XhoI fragment from pCGN526 by digesting with XhoI and religating.

pCGN149a was made by cloning the BamHI-kanamycin gene fragment from pMB9KanXXI into the BamHI site of pCGN148a. pMB9KanXXI is a pUC4K variant (Vieira and Messing, *Gene* (1982) 19:259-268) which has the XhoI site missing, but contains a functional kanamycin gene from Tn903 to allow for efficient selection in Agrobacterium.

pCGN149a was digested with HindIII and BamHI and ligated to pUC8 digested with HindIII and BamHI to produce pCGN169. This removed the Tn903 kanamycin marker. pCGN565 and pCGN169 were both digested with HindIII and PstI and ligated to form pCGN203, a plasmid containing the CaMV 35S promoter and part of the 5'-end of the TN5 kanamycin gene (up to the PstI site, Jorgenson et. al., (1979), supra). A 3'-regulatory region was added to pCGN203 from pCGN204 (an EcoRI fragment of CaMV (bp 408-6105) containing the region VI 3' cloned into pUC18 (Yanisch-Perron, et al., *Gene* (1985) 33:103-119) by digestion with HindIII and PstI and ligation. The resulting cassette, pCGN206, was the basis for the construction of pCGN986.

The pTiA6 T-DNA tml 3'-sequences were subcloned from the Bam19 T-DNA fragment (Thomashow et al., (1980) supra) as a BamHI-EcoRI fragment (nucleotides 9062 to 12,823, numbering as in Barker et al., *Plant Mol. Biol.* (1982) 2:335–350) and combined with the pACYC184 (Chang and Cohen (1978), supra) origin of replication as an EcoRI-HindIII fragment and a gentamycin resistance marker (from plasmid pLB41), obtained from D. Figurski) as a BamHI-HindIII fragment to produce pCGN417.

The unique SmaI site of pCGN417 (nucleotide 11,207 of the Bam19 fragment) was changed to a SacI site using linkers and the BamHI-SacI fragment was subcloned into pCGN565 to give pCGN971. The BamHI site of pCGN971 was changed to an EcoRI site using linkers. The resulting EcoRI-SacI fragment containing the tml 3' regulatory sequences was joined to pCGN206 by digestion with EcoRI and SacI to give pCGN975. The small part of the Tn5 kanamycin resistance gene was deleted from the 3'-end of the CaMV 35S promoter by digestion with SalI and BglII, blunting the ends and ligation with SalI linkers. The final expression cassette pCGN986 contains the CaMV 35S promoter followed by two SalI sites, an XbaI site, BamHI, SmaI, KpnI and the tml 3' region (nucleotides 11207–9023 of the T-DNA).

The 35S promoter-tml 3' expression cassette, pCGN986 was digested with HindIII. The ends were filled-in with Kleenow polymerase and XhoI linkers added. The resulting plasmid was called pCGN986X. The BamHI-SacI fragment of pBRX25 containing the nitrilase gene was inserted into BamHI-SacI digested pCGN986X yielding pBRX66.

Construction of pBRX25 is described in European application EPA 0 229 042 filed Jan. 7, 1987, which application is incorporated herein by reference. Briefly, the method was as follows: The nucleotide sequence of a 1212-bp PstI-HincII DNA segment encoding the bromoxynil-specific nitrilase contains 65-bp of 5' untranslated nucleotides. To facilitate removal of a portion of these excess nucleotides, plasmid pBRX9 was digested with PstI, and treated with nuclease Bal31. BamHI linkers were added to the resulting ends. BamHI-HincII fragments containing a functional bxn gene were cloned into the BamHI-SmaI sites of pCGN565. The resulting plasmid, pBRX25, contains only 11 bp of 5' untranslated bacterial sequence.

pBRX66 was digested with PstI and EcoRI, blunt ends generated by treatment with Kleenow polymerase, and XhoI linkers added. The resulting plasmid pBRX68 now has a tml 3' region that is approximately 1.1 kb. pBRX68 was digested with SalI and SacI, blunt ends generated by treatment with Kleenow polymerase and EcoRI linkers added. The resulting plasmid, pCGN986XE is a 35S promoter—tml 3' expression cassette lacking the nitrilase gene.

The Tn5 kanamycin resistance gene was then inserted into pCGN986XE. The 1.0 kb EcoRI fragment of pCGN1536 (see below) was ligated into pCGN986XE digested with EcoRI. A clone with the Tn5 kanamycin resistance gene in the correct orientation for transcription and translation was chosen and called pCGN1537b. The 35S promoter Kan$^R$-tml 3' region was then transferred to a chloramphenical resistant plasmid backbone. pCGN786 (a pUC-CAM based vector with the synthetic oligonucleotide 5' GGAATTCGTCGACAGATCTCTGCAGCTCGAGGGATCCAAGCTT 3' containing the cloning sites EcoRI, SalI, BglII, PstI, XhoI, BamHI, and HindIII inserted into pCGN566) was digested with XhoI and the XhoI fragment of pCGN1537b containing the 35S promoter—Kan$^R$-tml 3' region was ligated in. The resulting clone was termed pCGN1546.

pCGN1536 Construction.

The 5.4 kb EcoRI fragment is removed from pVK232 (Knauf and Nester, *Plasmid* (1982)8:45), by EcoRI digestion and cloned into EcoRI digested pACYC184 (Chang and Cohen, *J. Bacteriol.* (1978) 134:1141–1156) to create pCGN14. The 1434 bp ClaI-SphI fragment of pCGN14, containing the mas 5' region (bp20128–21562 according to numbering of (Barker et al., *Plant Mo. Biol.* (1983) 2:335–350) is cloned into AccI-SphI digested pUC19 (Yanisch-Perron et al., *Gene* (1985) 33:103–119) to generate pCGN40. A 746 bp EcoRV-NaeI fragment of the mas 5' region is replaced by an XhoI site by digesting pCGN40 with EcoRV and NaeI followed by ligation in the presence of a synthetic XhoI linker DNA to create pCGN1036. The 765 bp SstI-HindIII fragment (bp 18474–19239) of pCGN14, containing the mas 3' region, is cloned into SstI-HindIII digested pUC18 (Yanish-Perron et al., *Gene* (1985) 33:103–119) to yield pCGN43. The HindIII site of pCGN43 is replaced with an EcoRI site by digestion with HindIII, blunt ending with Klenow enzyme, and ligation of synthetic EcoRI linker DNA to create pCGN1034. The 767 bp EcoRI fragment of pCGN1034 is cloned into EcoRI-digested pCGN1036 in the orientation that places bp 19239 of the mas 3' region proximal to the mas 5' region to create pCGN1040. pCGN1040 is subjected to partial digestion with SstI, treated with T4 DNA polymerase to create blunt ends, and ligated in the presence of synthetic XhoI linker DNA; a clone is selected in which only the SstI site at the junction of bp 18474 and vector DNA (constructed in pCGN43 and carried into pCGN1040) is replaced by an XhoI site to generate pCGN1047.

pCGN565 is digested with EcoRI and HindIII, treated with Klenow enzyme to create blunt ends, and ligated in the presence of synthetic XhoI linker DNA to create pCGN1003; this recreates the EcoRI site adjacent to the XhoI linker. pCGNI003 is digested with EcoRI, treated with Klenow enzyme to create blunt ends, and ligated in the presence of synthetic PstI linker DNA to create pCGN1007. The 1.5 kb XhoI fragment of pCGN1047, containing the mas 5' region and the mas 3' region with a multiple cloning site between, is cloned into XhoI digested pCGN1007 to construct pCGN1052. A portion of the multiple cloning site of pCGN1052 is deleted by digestion with XbaI and SstI, treated with Klenow enzyme to make blunt ends, and ligated to generate pCGN1052ΔXS.

The 1 kb EcoRI-SmaI fragment of pCGN550 (See pCGN783, Example II), containing the 1 ATG-kanamycin resistance gene, is cloned into EcoRI-SmaI digested Bluescript M13-KS (Strategene, Inc., Calif.) to create pBSKm; this plasmid contained an M13 region allowing generation of single stranded DNA. Single stranded DNA is generated according to the supplier's recommendations, and in vitro mutagenesis was performed (Adelman et al., DNA (1983) 2:183–193) using a synthetic oligonucleotide with the sequence 5'GAACTCCAGGACGAGGC3' to alter a PstI site with the kanamycin resistance gene and make it undigestable, creating pCGN1534. pCGN1534 is digested with SmaI and ligated in the presence of synthetic EcoRI linker DNA to generate pCGN1535.

The 1 kb EcoRI fragment of pCGN1535 is cloned into EcoRI digested pCGN1052ΔXS to create the mas5'-kan mas3' plant selectable marker cassette pCGN1536.

Construction of pCGN1541b pCGN65α2XX (see below) was digested with BglII and EcoRV, treated with Kleenow polymerase, and BglII linkers added. The resulting plasmid, pCGN65α2XX', now lacks an approximately 20 bp piece of DNA that was present in pCGNα2XX.

pBR322 (Bolivar et al., Gene (1977) 2:95-113) was digested with EcoRI and PvuII, treated with Kleenow polymerase to generate blunt ends, and BglII linkers added. An ampicillin resistant, tetracycline sensitive clone, pCGN1538 was selected. This clone now lacks the approximately 2.2 kb EcoRI-PvuII fragment containing the tetracycline resistance gene. The PvuII site has been lost but the EcoRI site was regenerated upon addition of BglII linkers.

pCGN65α2XX' was digested with BglII and ligated to BglII digested pCGN1538 to create pCGN1541a which contained both plasmid backbones. pCGN1541a was digested with XhoI and religated. An ampicillin resistant, chloramphenical sensitive clone was chosen which lacked the pACYC-184 derived backbone, creating pCGN1541b.

Construction of pCGN65α2XX pCGN451 consists of octopine synthase 5' non-coding region sequences 13,643 to 15,208 fused via an EcoRI linker to the 3' non-coding region sequences 11,207 to 12,823 of pTiA6 according to Barker et al., Plant Mol. Biol. (1983) 2:325. pCGN451 was digested with HpaI and ligated in the presence of synthetic SphI linker DNA to generate pCGN55. The XhoI-SphI fragment of pCGN55 (bp 13800-15208, including the right border, of Agrobacterium tumefaciens T-DNA; (Barker et al., Gene (1977) 2:95-113) was cloned into SalI-SphI digested of pUC19 (Yanisch-Perron et al., Gene (1985) 33:103-119) to create pCGN60. The 1.4 kb HindIII-BamHI fragment of pCGN60 was cloned into HindIII-BamHI digested with pSP64 (Promega, Inc.) to generate pCGN1039. pCGN1039 was digested with SmaI and NruI (deleting bp14273-15208; (Barker et al., Gene (1977) 2:95-113) and ligated in the presence of synthetic BglII linker DNA creating pCGN1039ΔNS. The 0.47 kb EcoRI-HindIII fragment of pCGN1039ΔNS was cloned in to EcoRI-HindIII digested pCGN565 to create pCGN565RB. The HindIII site of pCGN565RB was replaced with an XhoI site by HindIII digestion, treatment with Klenow enzyme, and ligation in the presence of synthetic XhoI linker DNA to create pCGN565RB-H+X.

pUC18 was digested with HaeII to release the lacZ' fragment, treated with Klenow enzyme to create blunt ends, and the lacZ'-containing fragment ligated into pCGN565RB-H+X, which had been digested with AccI and SphI and treated with Klenow enzyme, resulting in pCGN565RBα2X. In pCGN565RBα2X the orientation of lacZ' is such that the lac promoter is proximal to the right border. The clone is positive for lacZ' expression when plated on an appropriate host and contains bp 13990-14273 of the right border fragment (Barker et al. (1983) supra), having deleted the AccI-SphI fragment (bp 13800-13990). The 728 bp BglII-XhoI fragment of pCGN565RBα2X containing the T-DNA right border piece and the lacZ' gene, was cloned into BglII-XhoI digested pCGN65ΔKX-S+X, replacing the BglII-XhoI right border fragment of pCGN65ΔKX-S+X, to create pCGN65α2X.

Construction of pCGN65ΔKX-S+X pCGN501 was constructed by cloning a 1.85 kb EcoRI-XhoI fragment of pTiA6 (Currier and Nester, J. Bact. (1976) 126:157-165) containing bases 13362-15208 (Barker et al., Plant Mo. Biol. (1983) 2:335-350) of the T-DNA (right border), into EcoRI-SalI digested M13mp9 (Vieira and Messing, Gene (1983) 19:259-268). pCGN502 was constructed by cloning a 1.6 kb HindIII-SmaI fragment of pTiA6, containing bases 602-2212 of the T-DNA (left Border), into HindIII-SmaI digested M13mp9. pCGN501 and pCGN502 were both digested with EcoRI and HindIII and both T-DNA-containing fragments cloned together into HindIII digested pUC9 (Vieira and Messing, Gene (1982) 19:259-268) to yield pCGN503, containing both T-DNA border fragments. pCGN503 was digested with HindIII and EcoRI and the two resulting HindIII-EcoRI fragments (containing the T-DNA borders) were cloned into EcoRI digested pHC79 (Hohn and Collins, Gene (1980) 11:291-298) to generate pCGN518. The KpnI-EcoRI fragment from pCGN518, containing the left T-DNA border, is cloned into KpnI-EcoRI digested pCGN565 to generate pCGN580. The BamHI-BglII fragment of pCGN580 is cloned into the BamHI site of pACYC184 (Change and Cohen, J. Bacteriol. (1978) 134:1141-1156) to create pCGN51. The 1.4 kb BamHI-SphI fragment of pCGN60 (see pCGN65α2X section above) containing the T-DNa right border fragment, was cloned into BamHI-SphI digested pCGN51 to create pCGN65.

pCGN65 was digested with KpnI and XbaI, treated with Klenow enzyme to create blunt ends, and ligated in the presence of synthetic BglII linker DNA to create pCGN65ΔKX. pCGN65ΔKX was digested with SalI, treated with Klenow enzyme to create blunt ends, and ligated in the presence of synthetic XhoI linker DNA to create pCGN65ΔKX-S+X.

Final Construction of pCGN1558

The XhoI fragment of pCGN1546 containing the 35S promoter—Kan$^R$tml 3' region was cloned into XhoI digested 1541b to create pCGN1554. The XhoI fragment from pCGN1546 is oriented within 1541b such that the order of components is <left border—tml 3'—Kan$^R$—35S promoter—lacZ'> <right border.

The BglII fragment of pCGN1554 containing left border-tml3'-Kan$^R$-35S promoter-lacZ right border was cloned into BamHI restricted pCGN1532 (see below) resulting in the binary vector, pCGN1558. In pCGN1558, the orientation of the insert if such that the T-DNA left border is adjacent to the RI plasmid origin of replication. This binary vector has several advantages including a minimal mount of DNA between the T-DNA borders, high stability in Agrobacterium hosts, high copy number in E. Coli hosts and blue/white screen with multiple restriction enzyme sites for ease of cloning target DNA.

pCGN1532 construction.

The 3.5 kb EcoRI-PstI fragment containing the gentamycin resistance gene is removed from pPh1JI (Hirsch and Beringer, Plasmid (1984) 12:134-141) by EcoRI-PstI digestion and cloned into EcoRI-PstI digested pUC9 (Vieira and Messing, Gene (1982) 19:259-268) to generate pCGN549. HindIII-PstI digestion of pCGN549 yields a 3.1 kb fragment bearing the gentamycin resistance gene, which is made blunt ended by the Klenow fragment of DNA polymerase I and cloned into PvuII digested pBR322 (Bolivar et al., Gene (1977) 2:95–113) to create pBR322Gm. pBR322Gm was digested is DraI and SphI, treated with Klenow enzyme to create blunt ends, and the 2.8 kb fragment cloned into the Ri origin containing plasmid pLJbB11 (Jouanin et al., *Mol. Gen. Genet.* (1985) 201:370–374) which has been digested with ApaI and made blunt ended with Klenow enzyme, creating pLHbB11Gm. The extra ColE1 origin and the kanamycin resistance gene are deleted from pLJvB11GM by digestion with BamHI followed by self closure to create pGmB11. The HindII site of pGmB11 is deleted by HindII digestion followed by treatment with Klenow enzyme and self closure, creating pGmB11-H. The PstI site of pGmB11-H is deleted by PstI digestion followed by treatment with Klenow enzyme and self closure, creating pCGN1532.

6. Construction of EF-1α (Le-EFA)-GUS Construct and Plant Transformation a. Construction of pCGN2147—EF-1α 3' subclone for use in EF-1α cassette pCGN2141 was constructed by cloning the approximately 1.8 kb KpnI-PstI fragment of pCGN2134 into pUC19 cut with KpnI×PstI. This KpnI (FIG. 4, nucleotide #2771)—PstI fragment contains coding and 3' untranscribed regions. The approximately 1.0 kb BglII-PstI fragment of 2141 was cloned into Bluescript KSII (Stratagene) that has been digested with BamHI×PstI yielding pCGN2145. This BglII (FIG. 4, nucleotide #3619)—Pst fragment contains C-terminal coding regions and 3' untranscribed regions. The 1.0 kb SstI-EcoRI fragment of 2145 was cloned into SstI-EcoRI digested pCGN565 yielding pCGN2147.

b. Construction of 2140-EF-1α 5' Promoter Subclone For Use In EF-1α Cassette

In order to obtain desirable restriction sites for cloning in genes at the 3' end of a promoter fragment, a small fragment of the 5' region of EF-1α was amplified using polymerase chain reaction (PCR) (Perkin-Elmer, Cetus) thermal cycler, as per the manufacturer's instructions (including manufacturer's reagents) and oligonucleotides that add desired linkers. This small fragment was then rejoined with other 5' sequences to make a suitable promoter fragment. Specifically the oligos were:

EFp54

---HindIII

|---------|
5' CAG—CAG—AAG—CTT—GCT—GTA—GTT—GTT—
2135 ---

TAC—CAG 3'
2158

EFp56

---Sst              ---Sma

|-------|           |-------|
5' ACG—ACG—GAG—CTC—TCG—CCC—GGG---

---Xho

|-------|
—CAT—CTC—GAG—ACA—CTA—AGA—AAC
2450 ---

TGC—ATT—TAC—3'
2427

Figure 4J:
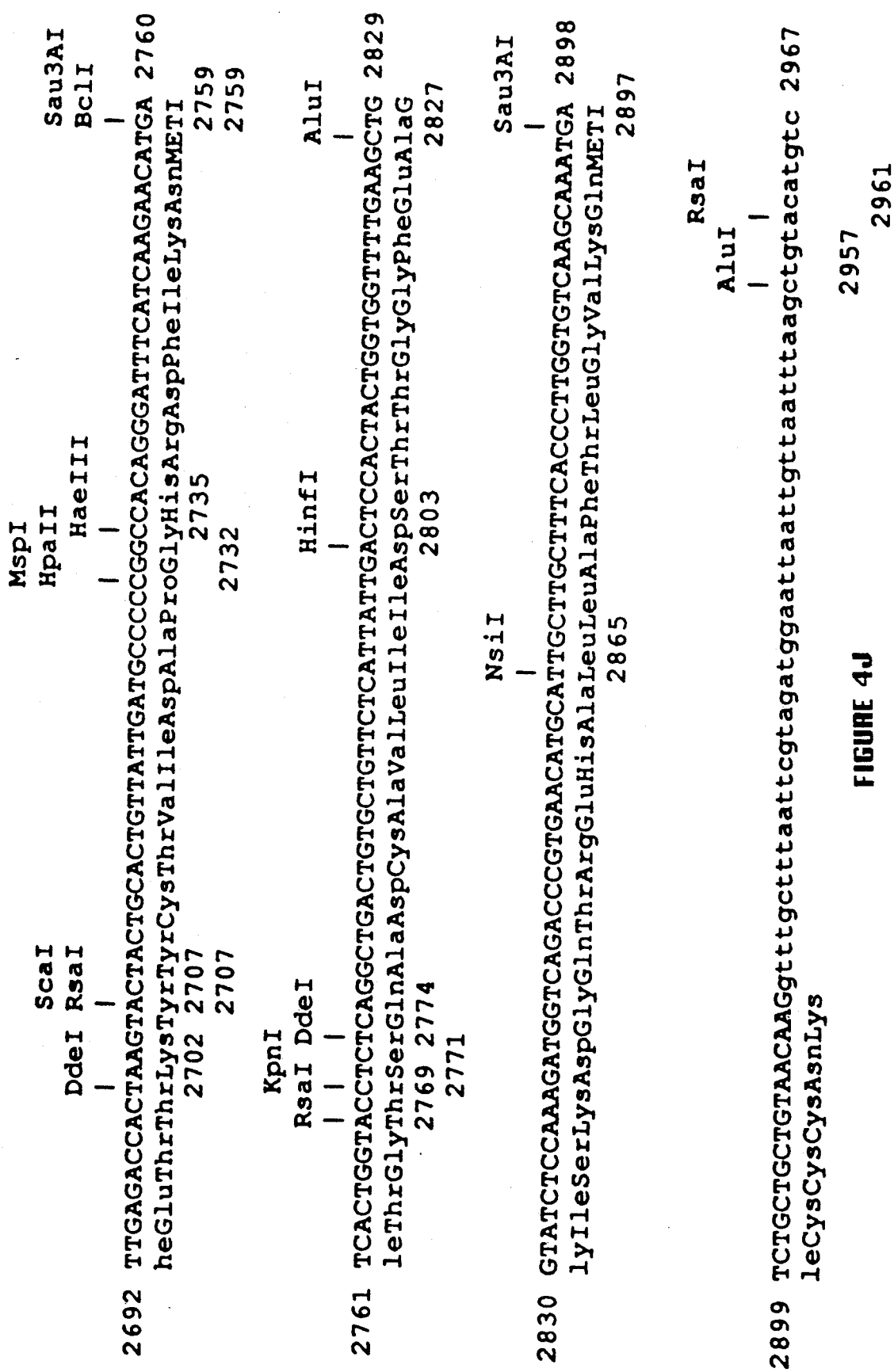
Figure 40:
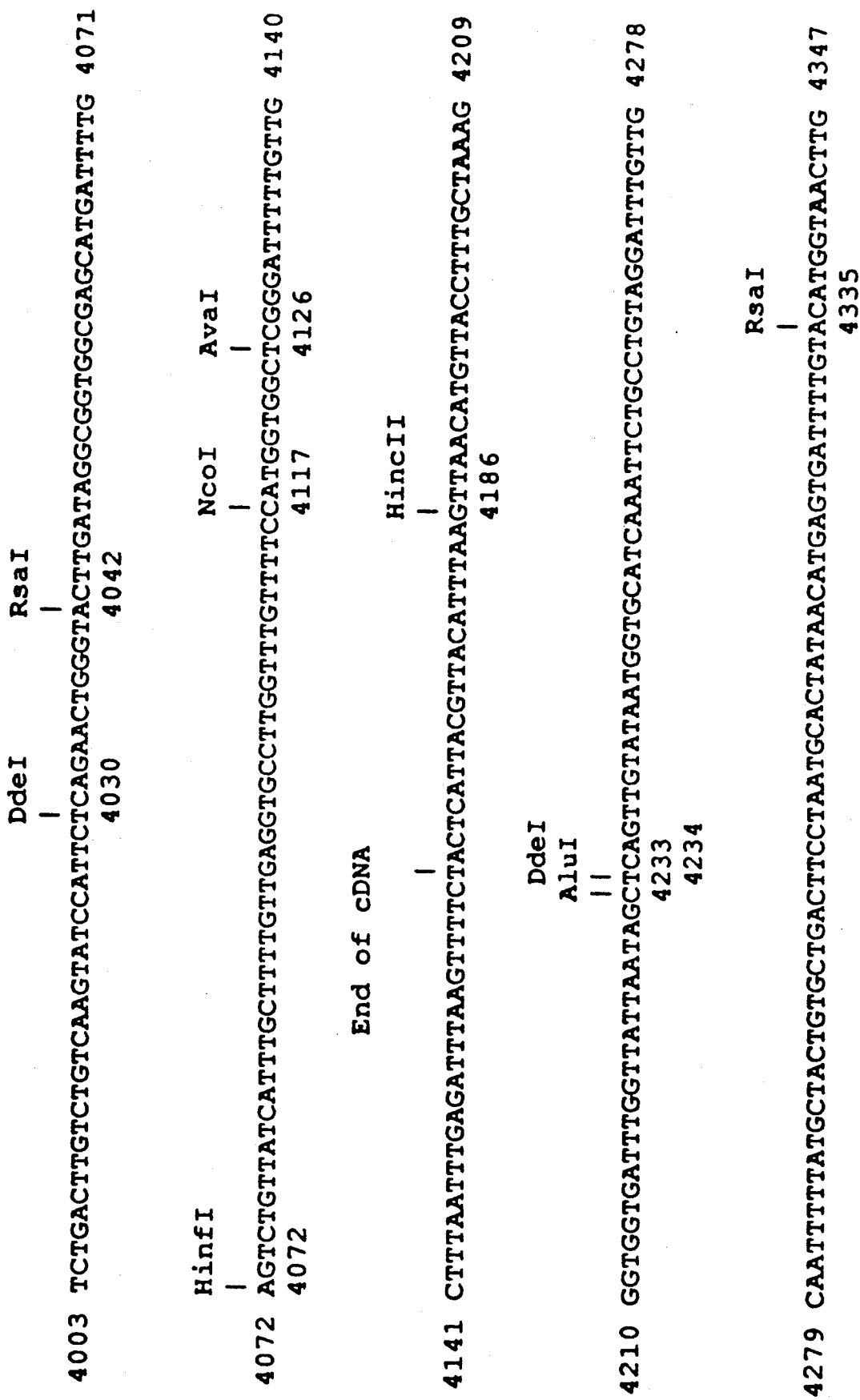
Figure 4P:
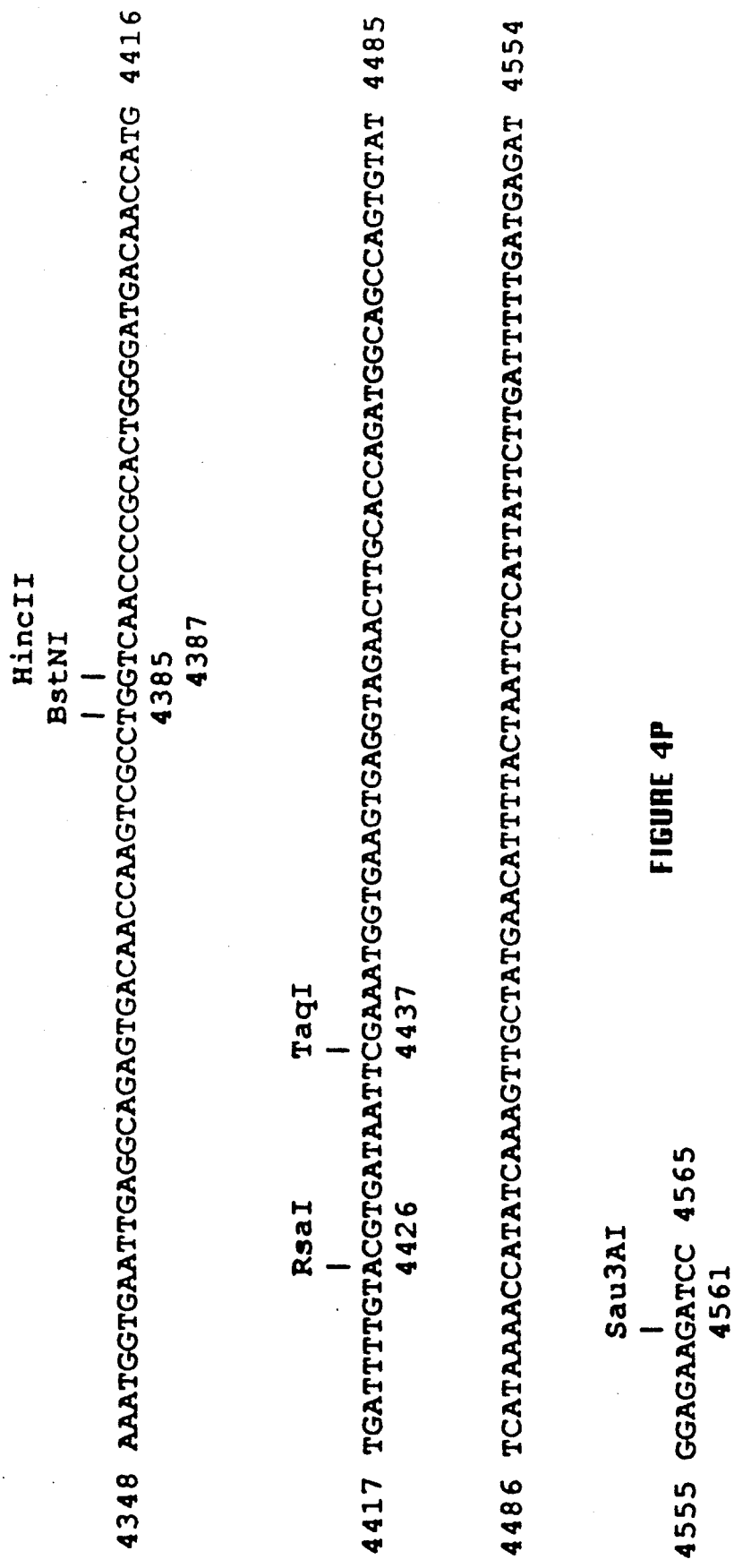

Specifically the reaction contained 53.5 μl H₂O, 10 μl 10xRxn buffer, 16 μl dNTP's [1.25 mM dCTP, dATP, dGTP & TTP], 5 μl EF-p54 (20 mM), 5 μl EF-p56 (20 mM), 20 μl pCGN675 (1 ng/μl), 0.5 μl TAQ polymerase. The resulting ≈300 bp fragment was restricted with HindIII and SstI and cloned into pUC12 Cm$^R$ (Buckley, Ph.D. thesis) that had been cut with HindIII and SstI. This resulted in pCGN2142. The sequence of the fragment in 2142 generated by PCR was determined and found to be identical to the same region in pCGN675 (See Example 3) (FIG. 4, nucleotide 190 2135 > 2450).

pCGN2137 was obtained by cutting pUC19 with HindIII, filling in with Kleenow polymerase and selecting for a clone that had lost the HindIII site.

The approximately 6.5 kb BamHI-KpnI (2771) fragment of pCGN675 was cloned into BamHI×KpnI cut pCGN2137 yielding pCGN2139. The BamHI-KpnI fragment in pCGN2139 contains 5' upstream regions and approximately 300 base pairs of N-terminal coding region. The approximately 9.5 kb HindIII-SstI fragment of 2139 was ligated to the approximately 300 bp HindIII-SstI fragment of pCGN2142 yielding pCGN2140. The approximately 6 kb EF-1α 5' fragment in 2140 contains 5' upstream and 5' untranslated regions but no coding sequences.

c. Construction of pCGN2148-EF-1α Cassette

The approximately 6 kb SphI-SstI fragment of 2140 containing the EF-1α promoter was cloned into SphI-Sst cut pCGN2147 yielding pCGN2148. This clone thus contains the approximately 6 kb 5' promoter fragment, the approximately 1 kb 3' EF-1α fragment and restriction sites in between into which genes can be cloned.

d. Construction of pCGN2154-EF-1α-GUS Chimera pCGN1804 (see Example II) contains the *E. coli* β-glucuronidase (GUS) gene. pCGN1804 was cut with EcoRI and the ends filled in with polymerase I (*Focus* (1984) 6:1 pg. 6). XhoI linkers were added and a clone with an XhoI site was selected and designated pCGN1805. The 1.8 kb SalI×XhoI fragment of pCGN1805 containing the GUS gene was cloned into XhoI digested pCGN2148. A clone with the GUS gene in the correct orientation for transcription and translation was selected and given the number pCGN2154.

e. Insertion of EF-1α GUS Chimera (pCGN2154) Into A Binary Vector (pCGN1558)

The approximately 9 kb PstI fragment of pCGN2154 containing EF-1α 5'-GUS-EF-1α3' was cloned into PstI cut pCGN1558 (see above). In pCGN2158 the 5'EF-1α-GUS EF-1α3' was inserted into pCGN1558 such that 5'EF-1α-GUS-EF-1α3' is transcribing in the same direction as the 35S-Kan-tml gene. In pCGN2157 the 5'EF-1α-GUS-EF-1α3' was inserted into pCGN1558 such that 5'EF-1α-GUS-EF-1α3' is transcribing in the opposite direction as the 35S-Kan-tml gene.

f. Preparation of Transgenic Plants

*Agrobacterium tumefaciens* strain 2760 (also known as LBA4404, Hoekerana et al., *Nature* (1983) 303:179–180) was transformed with pCGN2157 or pCGN2158 using the method of Holsters, et al., *Mol. Gen. Genet.*, (1978) 163:181–187. The transformed *A. tumefaciens* was then used in the cocultivation of plants.

Tomato

Tomato plants were transformed with *A. tumefaciens* LBA4404/pCGN2158 or pCGN2157, respectively, essentially as described in Example II. 6.b., with the exception that 500 mg/L of carbenicillin was used in the co-cultivation and regeneration procedure instead of the 350 mg/l cefotoxine described therein.

Tobacco

Tobacco leaf explants, roughly 5–10 mm by 5–10 mm, were cut from young leaves, approximately 3–5 cm long and third to sixth from the apex of *Nicotiana tobacum* cv. Xanthi which were grown under axenic conditions in solid medium: Murashige Minimal Organics (#1118 Gibco Laboratories, New York), 7% phytagar, 1 mg/l indole-3-acetic acid, 0.15 mg/l kinetin. The explants were plated on solid medium containing Murashige Minimal Organics, 6% phytagar, 40 mg/l adenine sulfate, 2 mg/l indole-3-acetic acid, 2 mg/l kinetin. A sterile #1 Whatman filter paper (Whatman Ltd., Maidstone, England) was placed on the top of the plate medium (explants are placed on top of filter) and they were incubated for 24 hours in the dark at 24° C.

The Agrobacterium were grown on AB medium (AB salts $K_2HPO_4$ 3 gm/l, $NaH_2PO_4 H_2O$ 1.15 g/l, $NH_4Cl$ 1 g/l, glucose 5 g/l, $FeSO_4$ 0.25 mg/l, $MgSO_4$ 0.246 mg/l, 0.14 mg/l, 15 g/l agar, 100 μg/l gentamycin sulfate and 100 μg/l streptomycin sulfate) for 4–5 days. Single colonies were inoculated into 5 mls of MG/L broth (50% Luria broth and 50% mannitol-glutamate salts medium (Garfinkel and Nester, J.Bacteriol. (1980)144:732–743)) and were incubated overnight in a shaker at 30° C. and 180 R.P.M. before co-cultivation.

Following the preincubation period, the explants were dipped into the bacterial suspension of $3.3 \times 10^8$ cells/ml for approximately 5 minutes, blotted on sterile paper towels and replated on the same plates. After 48 hours, the explants were placed on selection medium containing the same plate medium as above plus 350 mg/l cefotaxime and 100 mg/l kanamycin. The explants were transferred to fresh media every 2 weeks. At the 6 week transfer thereafter, shoot and green callus were trimmed from explants and placed on solid media: Murashige Minimal Organics, 0.5 mg/l indole-3-acetic acid, 2 mg/l kinetin, 40 mg/l adenine sulfate, 350 mg/l cefotaxime, 100 mg/l kanamycin. Shoots were harvested beginning about 4 weeks after co-cultivation and placed in 50 ml culture tubes with 25 ml of solid medium (7% bactagar 1 mg/l indole-3-butyric acid, 350 mg/l cefotaxime, 100 mg/l kanamycin) and grown at 24°–28° C., 12 hours light, 12 hours dark, light intensity 80–100 $uEm^{-2}s^{-1}$. Shoots root in 1–2 weeks and were then transplanted into soil and placed in growth chambers.

B. Results

1. Characterization of EF-1α Genomic Clone A (LeEF-A)

This sequence, comprising 4565 nucleotides in total is presented in FIG. 4. Notable features of the sequence include:

a. The EF-1α gene A has 2 introns (indicated in small letters). One occurs in the 5' untranslated region between nucleotides 43 and 44 of the cDNA (pCGN666). This intron spans nucleotides 1680–2436 of this sequence. The second intron occurs in the coding region between amino acids 154 and 155. This intron spans nucleotides 2916–2995.

b. The 5' upstream region of the LeEF-A gene is rather rich in A/T. The 2453 nucleotides upstream of the initiation ATG are 75.1% A/T. When the intron within this region (757 nucleotides) is examined, it is found to be 70.4% A/T. This contrasts to the 1347 nucleotides in the coding region (excluding intron 2) which shows 52.2% A/T.

2. GUS Analysis of pCGN2157/pCGN2158 Transformed Plants

Transformed tobacco plants were maintained in vitro on media containing 0.7% Phytagar (Gibco), Murashige and Skoog salts, 3% sucrose, 1 mg/LIAA, and 0.15 mg/L kinetin, pH 5.5. Transformed tomato plants were maintained in vitro on media containing 0.65% Phytagar, Murashige and Skoog salts, 1× Nitsch vitaimins (Nitsch, C. and Nitsch, J. P. (1967) Planta (Berl) 72:355–370), 0.15 mg/L kinetin, pH 6.0.

a. Flurometric Analysis

Analysis was performed on very young tobacco shoot tips. Shoot tips, weighing approximately 50–100 mg were quick frozen in liquid nitrogen and stored at −70° C. until assayed. Samples were ground in 500 μl GUS extraction buffer as described in Example II.7. In addition, protein concentration was determined on a separate aliquot using the Bio-Rad Protein Assay Kit (Bio-Rad) with Bovine Serum Albumin as standards. The data was then converted to pmole MU/min/mg protein.

b. Localization of GUS Activity Within Tissue

In situ GUS analysis was performed with X-glucuronic acid (Molecular Probes, Inc., Oreg.) as described in (Jefferson, *Plant Mol. Biol. Reporter* (1987) 5:387–405). For the tobacco shoot tip, free hand sections approximately 10–20 cell layers thick were made and immersed in staining solution overnight at 37° C. For tomato root tips, young roots were immersed in staining solution overnight at 37° C.

3. Expression Of EF-1α Gene A-GUS Chimera

To determine the pattern of expression of the EF-1α-GUS chimera, in situ hybridizations were performed using X-glucuronic acid. The action of B-glucuronidase on X-glucuronic acid gives rise to a blue colored compound.

A young root tip from a pCGN2157 tomato plantlet and a pCGN7001 (mas-GUS chimera—See Example II) plantlet were examined and compared. In the pCGN7001 root tip, development of color is seen throughout the root. In the pCGN2157 root, the main color development is seen in the very tip of the root. When endogenous EF-1α expression was analyzed in tomato root tips by 35S—RNA in situ hybridization (See, Example 1 and Pokalsky et al., (1989) *Nuc. Acids Res.*, 17:4661–4673) the majority of the hybridization was seen in the very root tip (1st 1–2 mm). The expression seen with pCGN2157 is similar and correlates with the rapid growth that is taking place in the root tip.

A shot tip from a pCGN2157 tobacco plant was sectioned and treated with X-glucuronic acid. The development of color is seen in the very apex of the shoot, the procambium, and the axillary buds. These regions are characterized by rapidly dividing cells. This indicates that the pattern for the EF-1α-GUS chimera correlates with area of rapid cell division.

Figure 5:
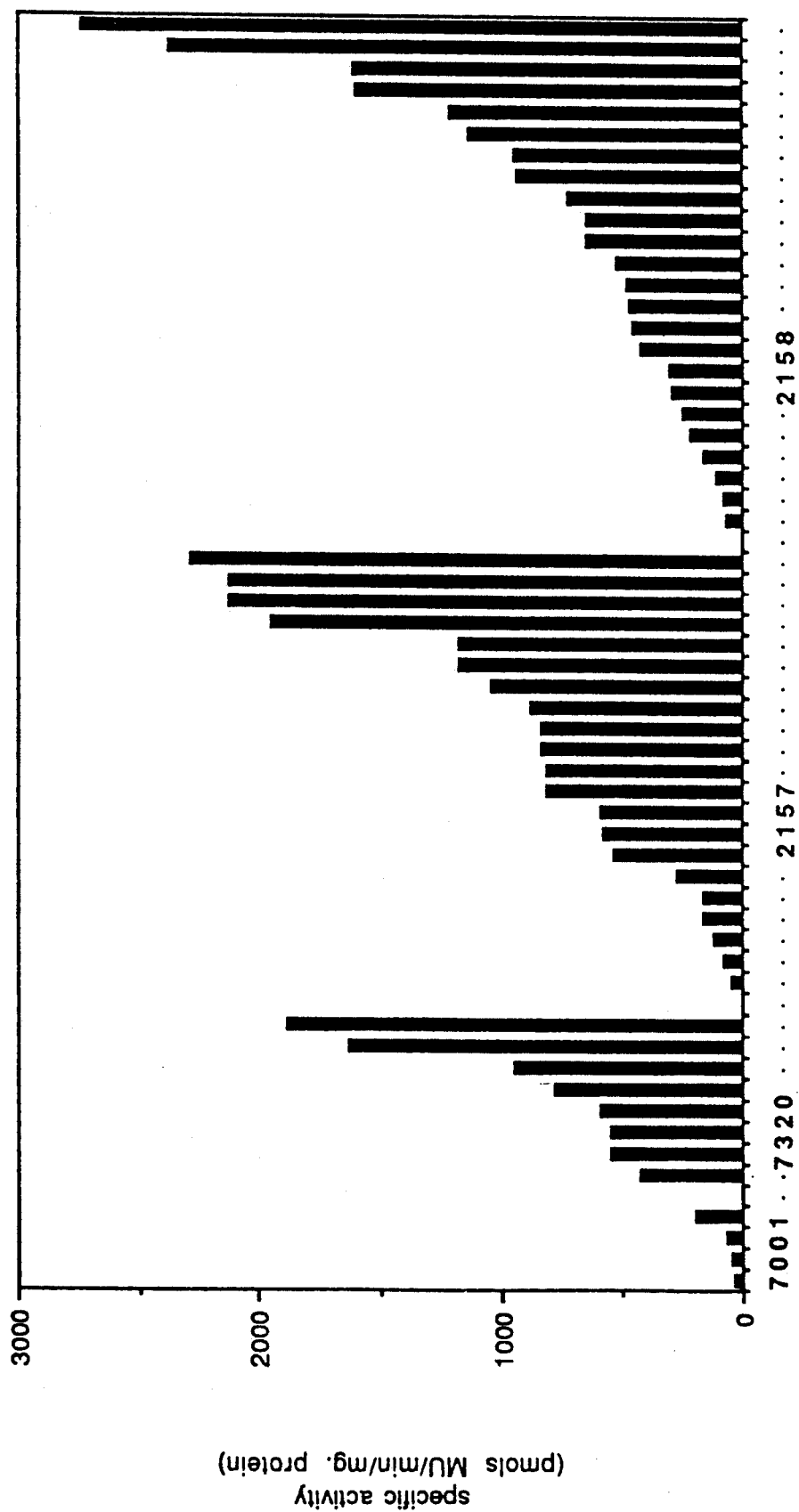
FIG. 5 is a graph representing a comparison of expression levels of various constructs of a flurometric GUS assay in transformed tobacco plants. Two EF-1α-GUS constructs (pCGN2157 and pCGN2158) are represented and compared to a mas-GUS construct (pCGN7001) and repeated testing of a single double 35S-GUS clone (pCGN7320).

Levels of expression were analyzed by looking at GUS levels in young shoot tips. Twenty pCGN2157 and twenty-four pCGN2158 tobacco plants were analyzed (See, FIG. 5). Expression levels of tested events were compared to different pCGN7001 tobacco plant events (mas-GUS chimera, See, Example II) and against pCGN7320 repeated testing of a clonal transformation event, clone pCGN7320 (double 35S-GUS chimera). The "2157" and "2158" plants showed GUS levels similar to or higher than the "d35S" plant and significantly higher than the "mas plants." Mas is known to be a relatively low level expresser (See, Example II) while d35S promoters give relatively high level expression (Kay et al. (1987) *Science*, 236:1299–1302). The level of expression from observed pCGN2157 and pCGN2158 correlate well with the fact that EF-1α genomic clone A is high expressing EF-1α gene.

It is evident from the above results, that plant cells and plants can be produced which have improved properties or may produce a desired product. In accordance with the subject invention, rapidly dividing cells can provide for high levels of a desired product, which may impart resistance of the plant to a wide variety of environmental hazards, such as herbicides, pests, heat, drought, disease, other forms of stress, and the like. In addition, the rate of growth of the plant may be modulated, so that higher or lower growth rates can be achieved, depending upon the particular situation. In this manner, crops may be grown more efficiently, in the substantial absence of weeds, may be less subject to attack by pathogens, so as to provide for enhanced productivity and greater efficiency in utilization of land and chemical resources, and the like. The subject constructs provide for enhanced expression of the particular gene in rapidly dividing cells, so as to reduce the level of expression in those parts of the plant where the expression product is not efficiently utilized. This provides for more efficient utilization of plant energy and resources, so that the energy and resources may be directed to a product of interest.

All publications and patent applications mentioned in this specification are indicative of the level of skill of those skilled in the art to which this invention pertains.

All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method to preferentially expose rapidly dividing plant cells to an expression product as distinct from other plant cells, said method comprising, growing a plant comprising cells containing a DNA construct integrated in the genome of said cells, said DNA construct comprising as operably joined components, in the 5' to 3' direction of transcription, a tomato elongation factor-1α transcriptional initiation region, a tomato elongation factor-1α translational initiation region, a foreign DNA sequence, and a transcriptional termination region functional in a plant.

2. A method according to claim 1 wherein said plant comprising cells is a tomato plant.

* * * * *